(12) United States Patent
Seon

(10) Patent No.: US 7,691,374 B2
(45) Date of Patent: Apr. 6, 2010

(54) METHOD FOR INCREASING THE EFFICACY OF ANTI-TUMOR AGENTS BY ANTI-ENDOGLIN ANTIBODY

(75) Inventor: Ben K. Seon, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 240 days.

(21) Appl. No.: 11/509,873

(22) Filed: Aug. 25, 2006

(65) Prior Publication Data

US 2007/0071761 A1    Mar. 29, 2007

Related U.S. Application Data

(63) Continuation-in-part of application No. 10/691,051, filed on Oct. 22, 2003, now Pat. No. 7,097,836.

(60) Provisional application No. 60/420,611, filed on Oct. 23, 2002.

(51) Int. Cl.
 *A61K 39/00* (2006.01)
 *A61K 39/395* (2006.01)
(52) U.S. Cl. .................. 424/133.1; 424/155.1
(58) Field of Classification Search ............ 424/133.1
 See application file for complete search history.

(56) References Cited

U.S. PATENT DOCUMENTS 5,660,827 A * 8/1997 Thorpe et al. ............ 424/152.1
6,190,660 B1 * 2/2001 Seon .................... 424/130.1
7,097,836 B1 * 8/2006 Seon .................... 424/133.1

FOREIGN PATENT DOCUMENTS

EP            0819430 A1 *  1/1998

OTHER PUBLICATIONS

Fundamental Immunology 242, William E. Paul, M.D. ed., 3rd ed. 1993.*
Takahashi et al. (Cancer Research 2001; 61: 7846-7854).*
Wiesenthal (http://weisenthal.org/feedback.html, Feb. 4, 2002).*
Tallarida (Drug Synergism and Dose-effect Analysis, Chapman & Hall/CRC, Boca Raton, 2000, pp. 1-13).*
Berenbaum ("Synergy, additivism and antagonism in immunosuppression," Clin exp Immunol 28:1-18, 1977).*
Biddle, et al.; In Vitro And In Vivo Cytotoxic Activity Of Anti-Human Leukemia Monoclonal Antibodies SN5c and SN6 Daunorubicin Conjugates; Leukemia Research, 1989; vol. 13, No. 8; pp. 699-707.
Bühring, et al.; Endoglin is Expressed on a Subpopulation of Immature Erythroid Cells of Normal Human Bone Marrow; Leukemia, Oct. 1991, vol. 5, No. 10; pp. 841-847.
Burrows, et al.; Up-Regulation of Endoglin on Vascular Endothelial Cells in Human Solid Tumors: Implications for Diagnosis and Therapy; Clinical Cancer Research, Dec. 1995, vol. 1; pp. 1623-1634.

Cheifetz, et al.; Endoglin Is a component of the Transforming Growth Factor-β Receptor System in Human Endothelial Cells; The Journal of Biological Chemistry, May 18, 1992, vol. 267, No. 27; pp. 19027-19030.
Fonsatti, et al.; Endoglin Is a Suitable Target for Efficient Imaging of Solid Tumors: In Vivo Evidence in a Canine Mammary Carcinoma Model; Clinical Cancer Research, May 2000, vol. 6; pp. 2037-2043.
Gougos, et al.; Identification of a Human Endothelial Cell Antigen With Monoclonal Antibody 44G4 Produced Against A Pre-B Leukemic Cell Line; The Journal of Immunology, Sep. 15, 1988, vol. 141, No. 6; pp. 1925-1933.
Haruta, et al.; Distinct human leukemia-associated cell surface glycoprotein GP160 defined by monoclonal antibody SN6; Proc. Natl. Acad. Sci. U S A, Oct. 1986, vol. 83; pp. 7898-7902.
Holmes; Paclitaxel Combination Therapy in the Treatment of Metast Breast Cancer: A Review; Seminars in Oncology, Oct. 1996, vol. 23, No. 5; pp. 46-56.
Lastres, et al.; Regulated expression on human macrophages of endoglin, an Arg-Gly-Asp- containing surface antigen; Eur. J. Immunol., 1992, vol. 22; pp. 393-397.
Li, et al.; Defective Angiogenesis in Mice Lacking Endoglin; Science, May 28, 1999, vol. 284(5419); pp. 1534-1537.
Matsuzaki, et al.; Effect Of Induced Transformation Of Human Leukemia Cells On The Expression Of GP160, A Novel Human Leukemia-Associated Cell Surface Glycoprotein; Fed. Proc. 46; p. 1056.
Matsuno, et al.; Induction of Lasting Complete Regression of Preformed Distinct Solid Tumors by Targeting the Tumor Vasculature Using Two New Anti-Endoglin Monoclonal Antibodies; Clinical Cancer Research, Feb. 1999, vol. 5; pp. 371-382.
Maier, et al.; In vitro inhibition of endothelial cell growth by the antiangiogenic drug AGM-1470 (TNP-470) and the anti-endoglin antibody TEC-11; Anti-Cancer Drugs; 1997, vol. 8; pp. 238-244.
Miller, et al.; Elevated expression of endoglin, a component of the TGF-β-receptor complex, correlates with proliferation of tumor endothelial cells; International Journal of Cancer, May 17, 1999, vol. 81; pp. 568-572.
Rokhlin, et al.; Differential Expression of Endoglin on Fetal and Adult Hematopoietic Cells in Human Bone Marrow; The Journal of Immunology, 1995; pp. 4456-4465.
Seon, et al.; CD105 Workshop: Immunohistochemical detection of CD105 in the vascular endothelium of human malignant and non-malignant tissues; In Leukocyte Typing VI: White Cell Differentiation Antigens, Garland Publishing, Inc., 1998; pp. 709-710.
Seon, et al.; Long-Lasting Complete Inhibition of Human Solid Tumors in SCID Mice by Targeting Endothelial Cells of Tumor Vasculature with Antihuman Endoglin Immunotoxin; Clinical Cancer Research, Jul. 1997, vol. 3; pp. 1031-1044.

(Continued)

*Primary Examiner*—Brandon J Fetterolf
(74) *Attorney, Agent, or Firm*—Hodgson Russ LLP

(57) ABSTRACT

The present invention provides a method for enhancing the efficacy of chemotherapeutic agents for therapy of cancer including tumors and other angiogenesis-associated diseases such as rheumatoid arthritis. The method comprises the steps of administering to an individual in need of treatment, a combination of an anti-endoglin antibody and a chemotherapeutic agent. The anti-endoglin antibody and the chemotherapeutic agent may be administered sequentially or concurrently.

6 Claims, 12 Drawing Sheets

OTHER PUBLICATIONS

Seon; Expression of Endoglin (CD 105) in Tumor Blood Vessels; Int. J. Cancer, 2002, vol. 99; pp. 310-311.

Tabata, et al.; Antiangiogenic Radioimmunotherapy of Human Solid Tumors in SCID Mice Using $^{125}$I-Labeled Anti-Endoglin Monoclonal Antibodies; Int. J. Cancer, 1999, vol. 82; pp. 737-742.

Takahashi, et al.; Antiangiogenic Therapy of Established Tumors in Human Skin/Severe Combined Immunodeficiency Mouse Chimeras by Anti-Endoglin (CD105) Monoclonal Antibodies, and Synergy between Anti-Endoglin Antibody; Cancer Research, Nov. 1, 2001, vol. 61; pp. 7846-7854.

Wang, et al.; A monoclonal Antibody Detects Heterogeneity in Vascular Endothelium of Tumours and Normal Tissues; Int. J. Cancer, 1993, vol. 54; pp. 363-370.

Weisenthal; Is one "sensitive" drug better than another? Can you detect drug synergy? What are the best drug combinations?; http://weisenthal.org/feedback.htm; Feb. 4, 2002; 2 pages.

* cited by examiner

*Synergistic effect

*Synergistic effect

METHOD FOR INCREASING THE EFFICACY OF ANTI-TUMOR AGENTS BY ANTI-ENDOGLIN ANTIBODY

This application is a continuation in-part of U.S. non-provisional application Ser. No. 10/691,051 filed on Oct. 22, 2003, now U.S. Pat. No. 7,097,836, which in turn claims priority to U.S. Provisional Patent Application No. 60/420,611 filed Oct. 23, 2002, the disclosures of which are incorporated herein by reference.

FIELD OF THE INVENTION

The present invention relates to the field of cancer therapy. In particular, the invention provides a method for increasing the efficiency of anti-tumor agents.

BACKGROUND OF THE INVENTION

Angiogenesis is the formation of new capillary blood vessels leading to neovascularization. It is a complex process which includes a series of sequential steps including endothelial cell-mediated degradation of vascular basement membrane and interstitial matrices, migration of endothelial cells, proliferation of endothelial cells, and formation of capillary loops by endothelial cells. Solid tumors are angiogenesis-dependent; i.e., as a small solid tumor reaches a critical diameter, for further growth it needs to elicit an angiogenic response in the surrounding normal tissue. The resultant neovascularization of the tumor is associated with more rapid growth, and local invasion. Further, an increase in angiogenesis is associated with an increased risk of metastasis. Accordingly, inhibiting tumor angiogenesis and associated tumor growth is an attractive approach to treating cancer for a variety of reasons (reviewed in 1-3). For example, antiangiogenic therapy can potentially overcome three major problems associated with other anticancer therapies, i.e., the problems of drug resistance (4, 5), poor delivery (6, 7) and tumor heterogeneity. Therefore, there is a need for effective methods of inhibiting angiogenesis and the tumor growth associated with it. One approach has been antibody-based targeting of tumor vasculature. By using specific antibodies to target vessels that supply tumors with blood, selective reduction of tumor tissue is possible, but not without undesirable complications.

Endoglin (EDG) has been targeted in antibody-based methods of reducing tumor vasculature, as EDG is a proliferation-associated antigen on endothelial and leukemia cells (8-11). Its expression is up-regulated in tumor-associated vascular endothelium (9-15). The EDG molecule is a homodimer glycoprotein antigen which was initially identified as a human leukemia-associated cell membrane antigen (16, 17). Its expression is restricted to immature B-lineage acute lymphoblastic leukemia cells, myelomonocytic leukemia cells, endothelial cells and a few minor normal cells (16-20). EDG binds transforming growth factor β (TGF-β), specifically to TGF-β1 and TGF-β3, but it does not bind to TGF-β2 (21).

Importantly, EDG is essential for angiogenesis (22). Certain anti-EDG monoclonal antibodies (mAbs) react with tumor-associated vascular endothelium more strongly than with vascular endothelium in normal tissues (9, 12-15). Immunoconjugates of selected anti-EDG mAbs that weakly cross-react with mouse endothelial cells are effective for suppressing angiogenesis and tumors in mice (10, 15, 23). These mAbs correspond to externally induced autoantibodies (24). Anti-EDG mAbs have been conjugated with deglycosylated ricin A-chain to obtain immunotoxins (10, 15) and with $^{125}$I to obtain radioimmunoconjugates (23). Although the anti-EDG immunotoxins showed strong antiangiogenic anti-tumor efficacy at the dose of 24 to 45% of the 50% lethal dose (LD50), they also exhibited strong toxicity in mice. For example, $LD_{50}$ of SN6f, SN6j and SN6k immunotoxins ranged between 14.8 and 17.8 μg/g body weight (10, 15). Therefore, the therapeutic windows of these immunotoxins are relatively narrow and are accordingly difficult to administer effectively and safely. Thus, there is a need for an alternative method of using anti-EDG antibodies to increase the effectiveness of anti-tumor agents in inhibiting angiogenesis and tumor growth.

SUMMARY OF THE INVENTION

It is an object of the present invention to enhance the efficacy of chemotherapeutic agents for therapy of cancer. The method comprises the steps of administering a combination of an anti-endoglin (EDG) antibody and a chemotherapeutic agent wherein the combination of anti-EDG antibody and chemotherapeutic agent has an unexpected synergistic anti-tumor effect. Any anti-EDG antibody or antigen binding fragment thereof can be used. Examples of suitable anti-tumor agents include, but are not limited to, cyclophosphamide (CPA), 5-fluorouracil, paclitaxel, methotrexate, cisplatin and doxorubicin. The effectiveness of the method of the present invention is demonstrated in severe combined immunodeficient (SCID) mice with human tumor xenografts. Antibodies and anti-tumor agents may administered by any method known to those skilled in the art, and the anti-EDG antibodies and the anti-tumor agent(s) may be administered concurrently or sequentially with the administration being repeated as necessary.

In one embodiment, data is presented demonstrating that combination of SN6j with a drug exerts synergistic antitumor efficacy in suppression of growth of colon cancer. This finding indicates that antiangiogenic therapy using our anti-EDG mAbs can be applied to many different types of solid tumors because anti-EDG mAbs do not target any particular tumor cells but target tumor blood vessels that are common to many different types of solid tumors.

Isotype-matched murine control IgG (IgG1-κ) and isotype-matched rat control IgG (IgG2a-κ) showed no significant staining. The staining patters were similar to that in A. Mouse and human skins in each panel are indicated by m and h, respectively.

Figure 2:
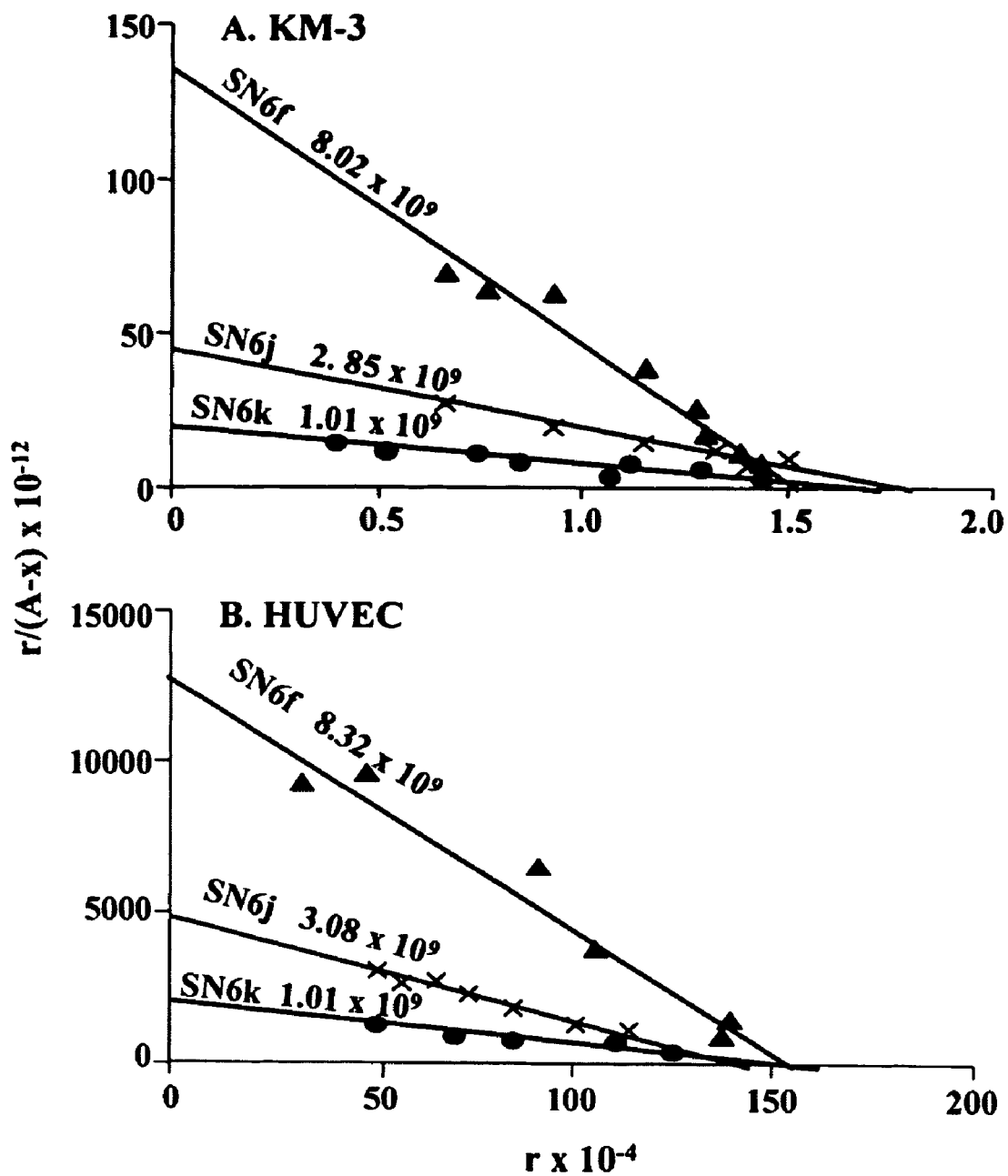

FIG. 2. Binding of $^{125}$I-labeled SN6f, SN6j and SN6k to EDG-expressing KM-3 cells (panel A) and HUVECs (panel B). r is the number of antibody molecules bound to one cell at a given dilution; A is the molar concentration of total antibody; and x is the molar concentration of bound antibody, so that (A-x) is the molar concentration of the free antibody. The slope of the binding curve gives the equilibrium constant, K. The intersection point between the binding curve and abscissa gives the maximum number of antibody molecules, n, that can be bound to a single cell. The equilibrium constant for the reaction, K, is expressed in liters per mole.

Figure 3:
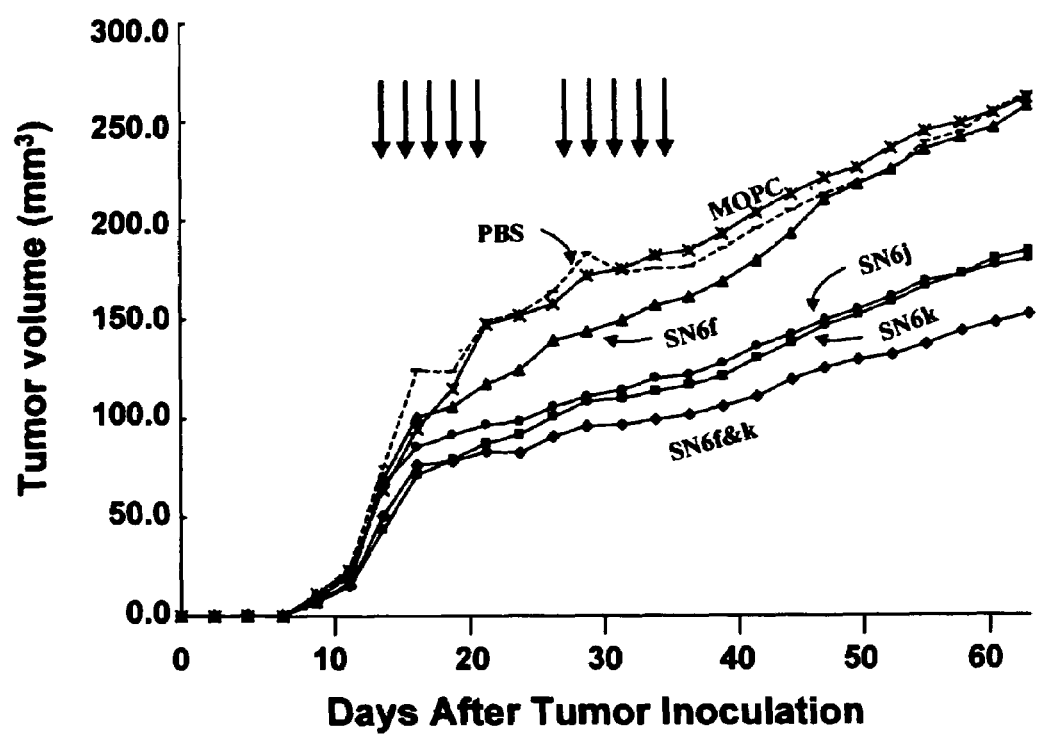

FIG. 3. Therapy of established tumors in human skin/SCID mouse chimeras by i.v. administration of naked anti-EDG mAbs. MCF-7 human breast cancer cells were injected into human skin grafts in SCID mice, and therapy was delayed until distinct palpable tumors appeared. Chimeras with distinct tumors were divided into groups [n=6 except for PBS (n=5) and MOPC (n=5) groups] and treated with PBS, an isotype-matched control IgG (MOPC), SN6f, SN6j, SN6k or SN6f plus SN6k. The therapy was performed in two cycles including one-week pause between the cycles to relieve the mice from the i.v. injection-associated stress. Each cycle consisted of five injections, at 2-days intervals, of PBS, a control IgG (200 µg), a mAb (200 µg) or a mixture of SN6f (200 µg) and SN6k (200 µg) as indicated in the figure. The arrows in the figure indicate injections of PBS, a control IgG, a mAb or a mixture of two mAbs.

Figure 4:
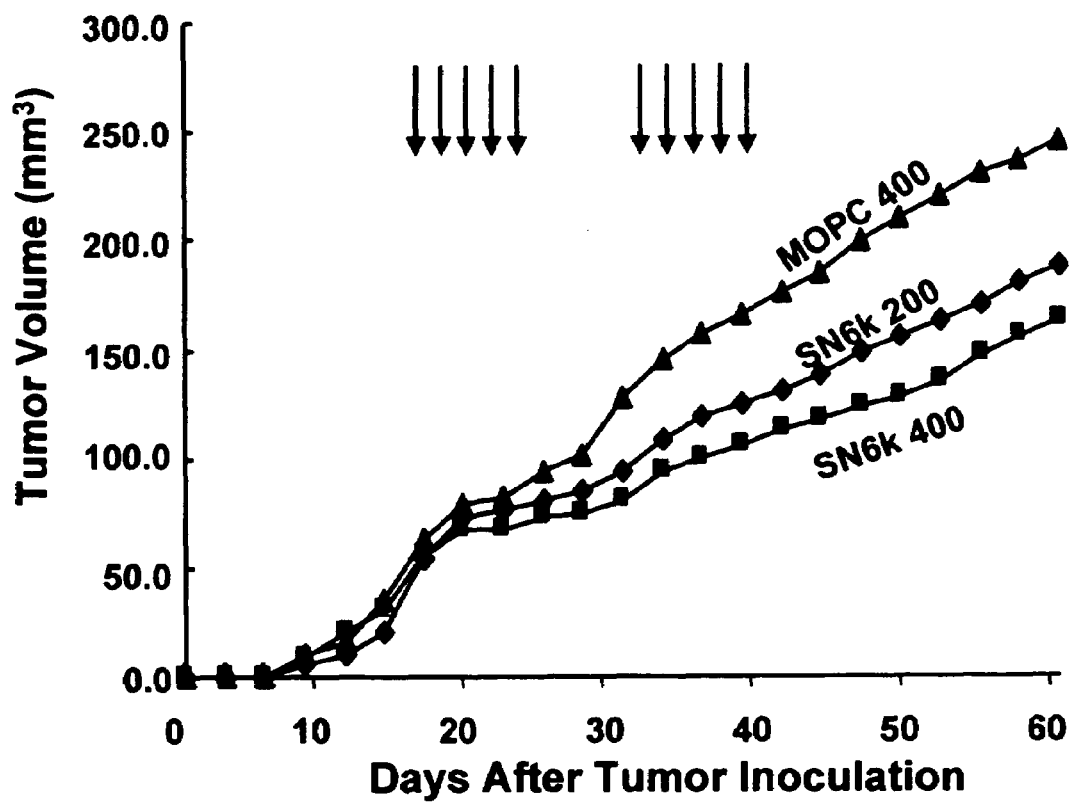

FIG. 4. Effect of different doses of SN6k on the anti-tumor efficacy. Established tumors in human skin/SCID mouse chimeras were generated as in FIG. 3. Groups of chimeras (n=6 in each group) were treated by i.v. administration of an isotype-matched control IgG (400 µg), 200 µg SN6k or 400 µg SN6k. Injections of the control IgG and SN6k were repeated as in FIG. 3.

Figure 5:
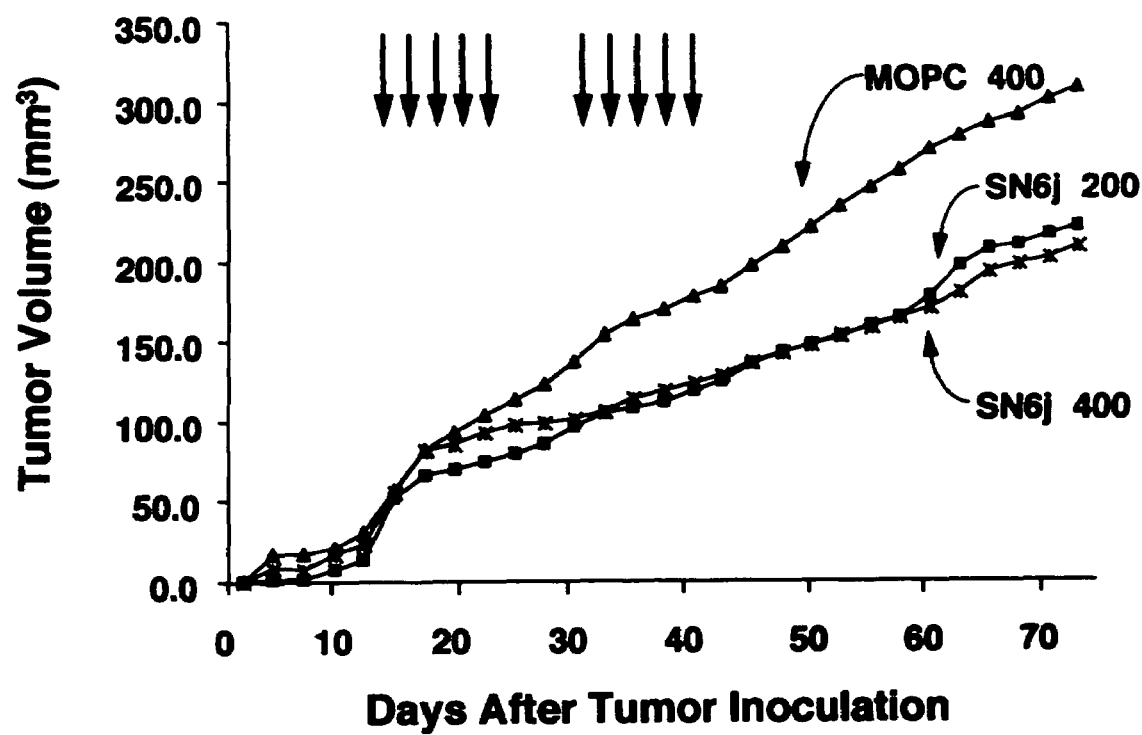

FIG. 5. Therapy of preformed tumors by systemic administration of different doses of SN6j. Three groups of chimeras bearing established tumors (n=6) were treated by i.v. administration of 400 µg of an isotype-matched control IgG, 200 µg SN6j or 400 µg SN6j. The arrows in the figure indicate injections of control IgG or SN6j.

Figure 6:
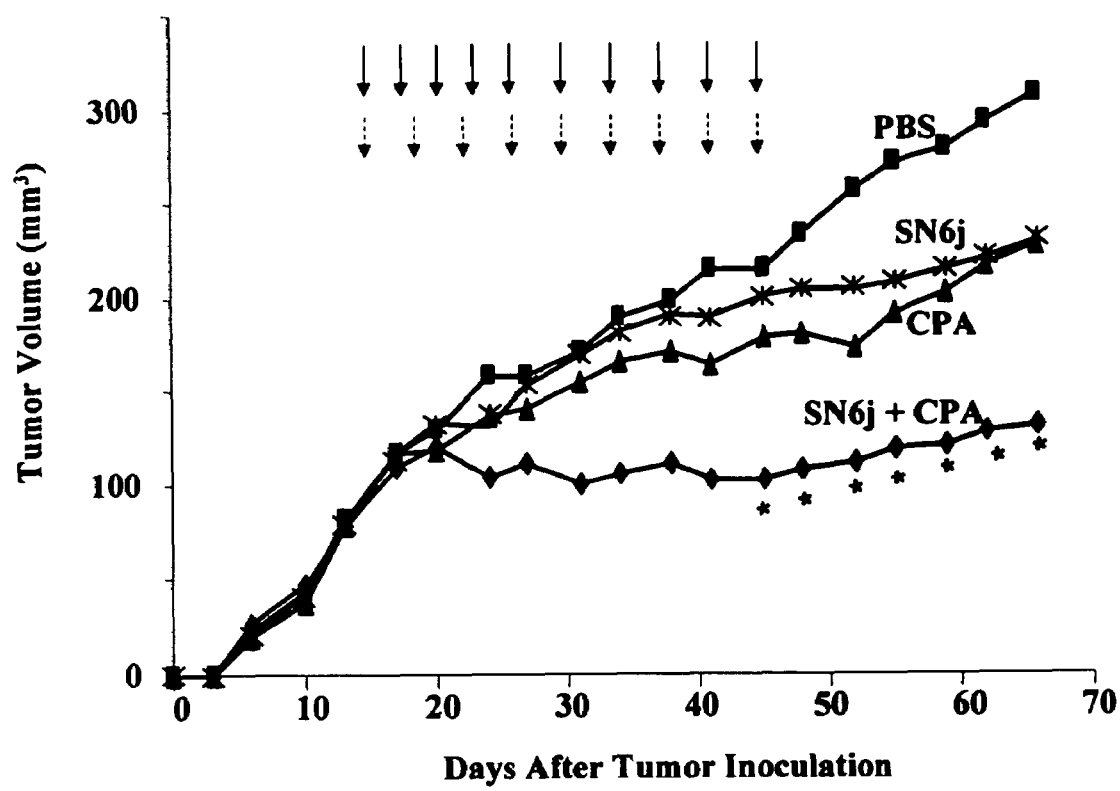

FIG. 6. Improved anti-tumor efficacy by the combination of an anti-EDG mAb with a chemotherapeutic drug and by using an antiangiogenic schedule of drug dosing. Established tumors of MCF-7 in human skin/SCID mouse chimeras were generated as described in FIGS. 3, 4 and 5. The solid arrows and dashed arrows indicate injections of SN6j and cyclophosphamide (CPA), respectively.

Figure 7:
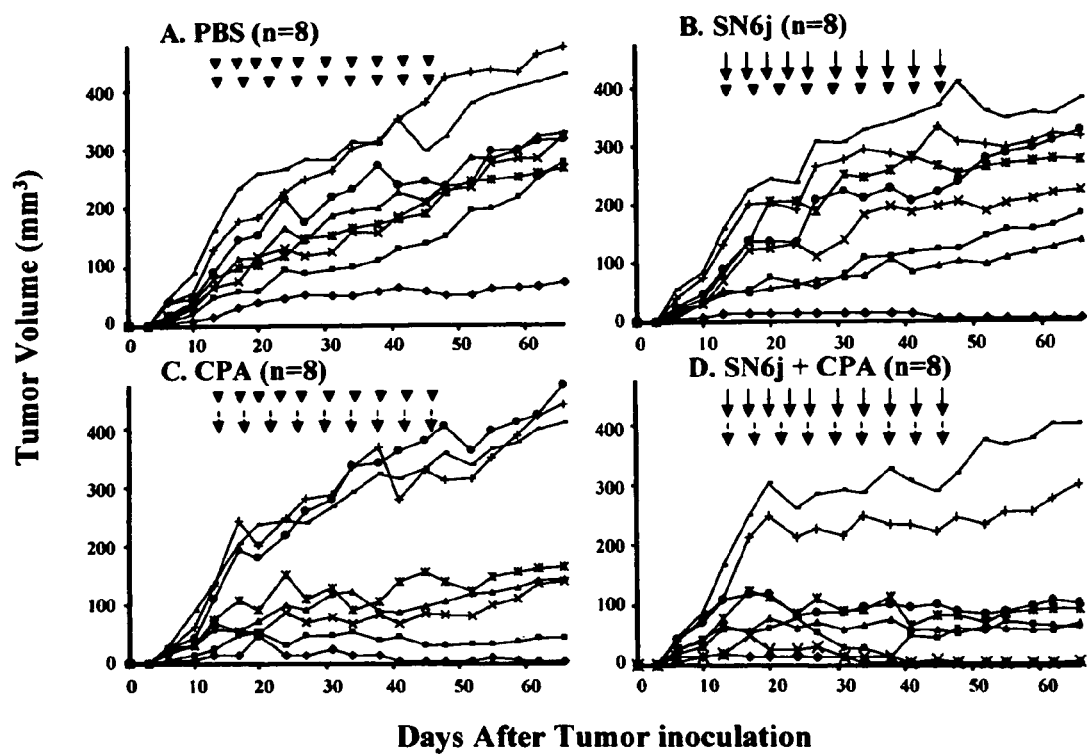

FIG. 7. Tumors in individual human skin/SCID mouse chimeras that were treated with PBS, SN6j, CPA, or SN6j plus CPA. Arrow heads, solid arrows and dashed arrows indicate injections of PBS, SN6j and CPA, respectively. Injections of PBS in panel A were performed i.v. (upper line) and i.p. (lower line) as controls of SN6j and CPA, respectively. PBS was injected i.p. as a control of CPA in panel B, whereas it was injected i.v. as a control of SN6j in panel C.

Figure 8:
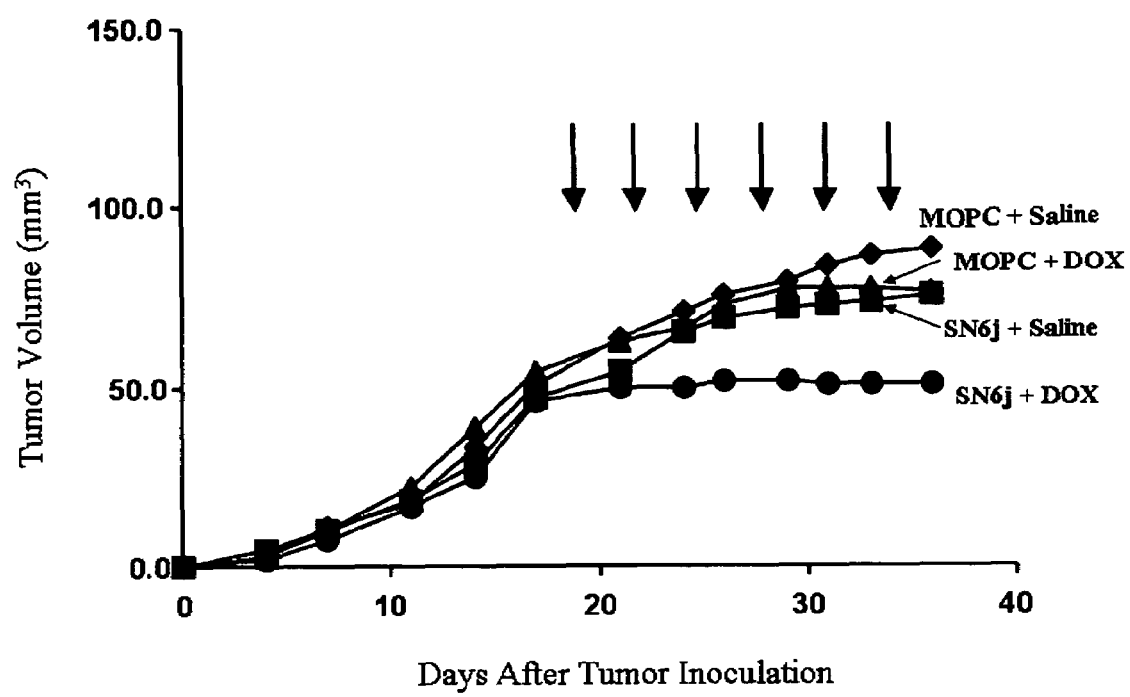

FIG. 8. Comparison of anti-tumor efficacy between SN6j and SN6j plus doxorubicin (DOX). MCF-7 human breast tumors in human skin/SCID mouse chimeras were generated as described in the legend to FIG. 3 and the chimeras bearing established tumors were distributed into four groups (n=7 except for the control IgG plus saline group for which n=6). An isotype-matched control IgG (MOPC 195 variant; IgG1-κ) plus saline (control of DOX), control IgG plus DOX, SN6j plus saline, or SN6j plus DOX were injected into tumor-bearing mice as indicated by arrows. SN6j and DOX showed synergistic anti-tumor efficacy as demonstrated in Table 2.

Figure 9:
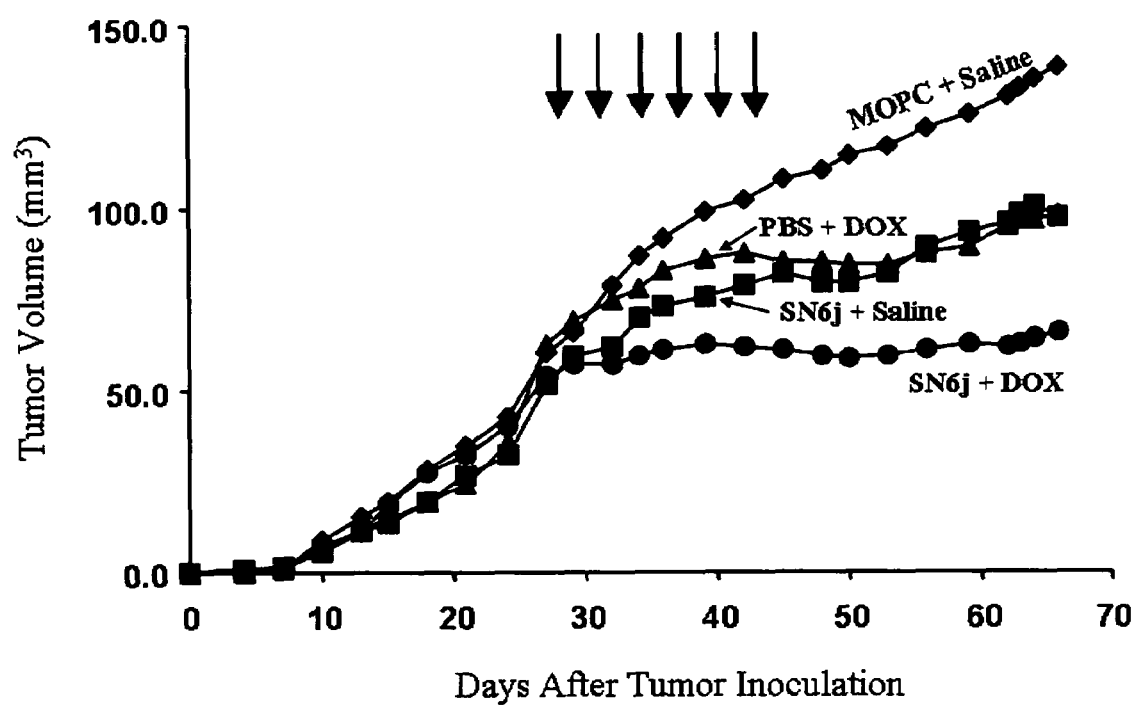

FIG. 9. Repeated test of comparison between SN6j and SN6j plus DOX for anti-tumor efficacy against established MCF-7 tumors. MCF-7 tumors in the human skin/SCID mouse chimeras were generated as described in FIG. 8 and the tumors were treated as described in FIG. 8 and as indicated by arrows. Results of FIG. 9 are consistent with those of FIG. 8.

Figure 10:
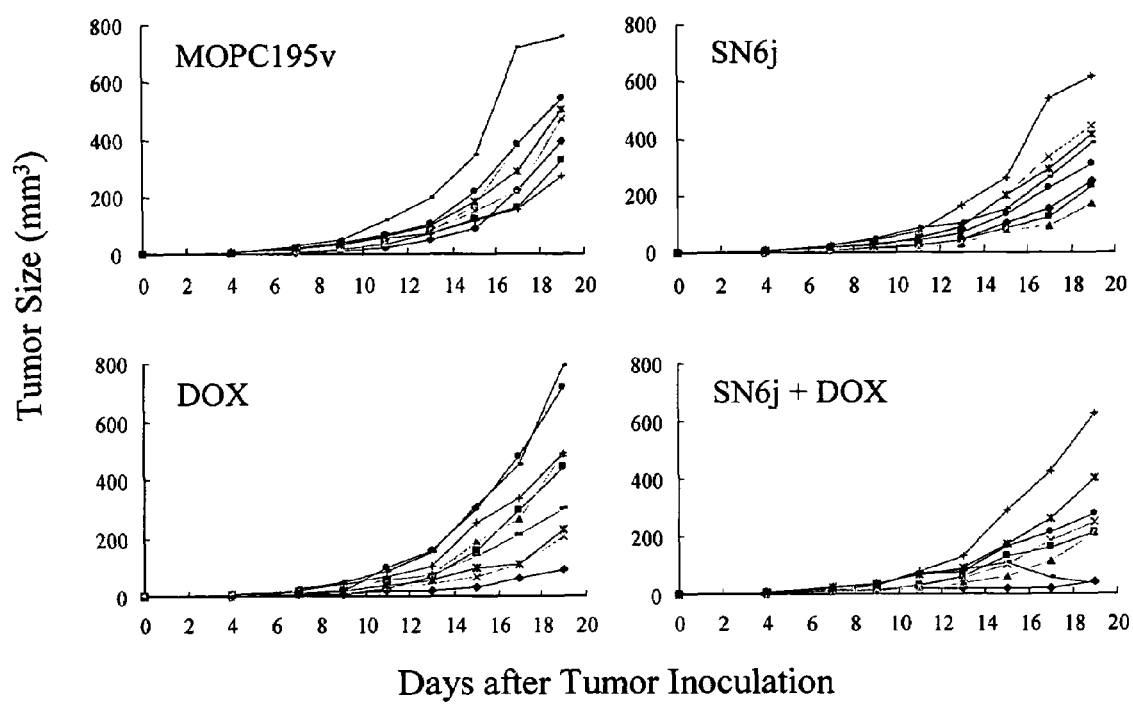

FIG. 10. Colon-26 tumors in individual BALB/c mice that were treated with an isotype-matched control IgG (MOPC195v), anti-endoglin monoclonal antibody (mAb) SN6j, doxorubicin (DOX) or SN6j plus DOX. Murine colorectal carcinoma colon-26 cells were inoculated subcutaneously into BLAB/c mice. Mice with typical subcutaneous tumors of a similar size were distributed evenly into four different groups at the onset of therapy. Mice with established tumors were treated by systemic administration of control IgG (MOPC195v, n=8), SN6j (n=8), DOX (n=9), or SN6j plus DOX (n=8).

Figure 11:
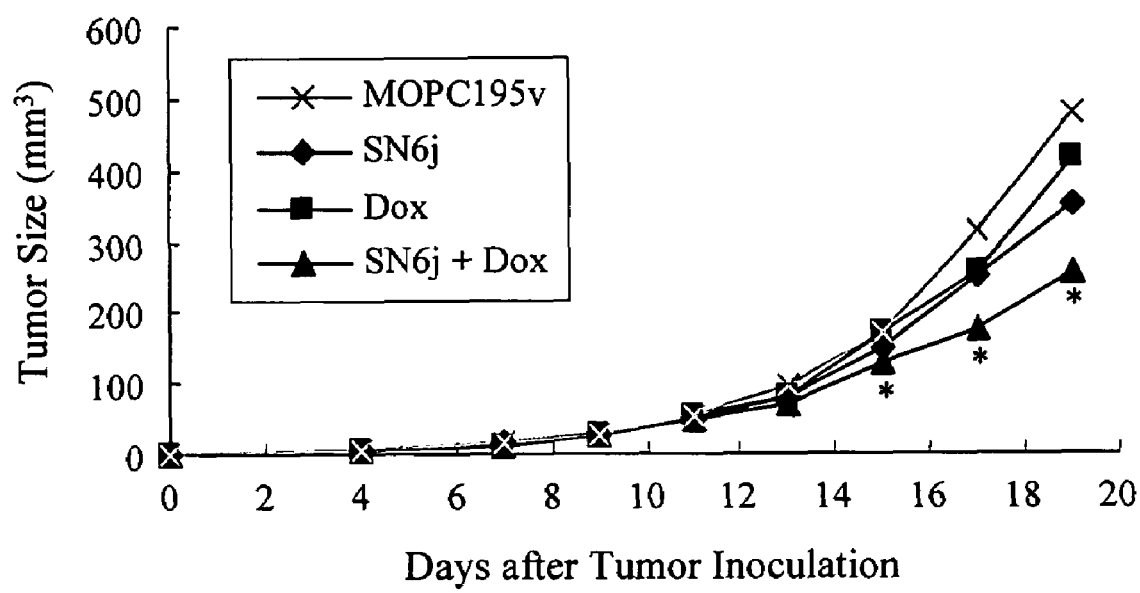

FIG. 11. Suppression of growth of established Colon-26 tumors by SN6j, DOX or SN6j plus DOX. Average tumor sizes in individual groups of mice in FIG. 10 are shown here. Analysis of the data (see Table 3) indicates that DOX plus SN6j exerted synergistic antitumor activities.

Figure 12:
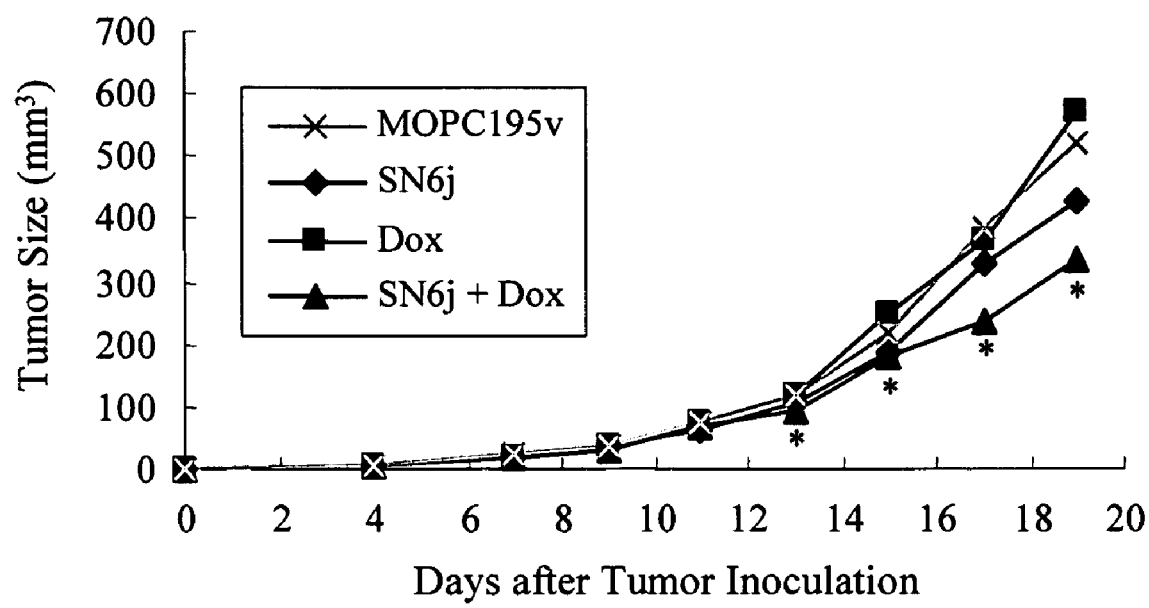

FIG. 12. Synergistic antitumor activity of SN6j plus DOX against groups of mice bearing larger tumors (larger than 4 mm$^3$). Mice bearing established Colon-26 tumors (see FIG. 10) were divided into two groups based on the size of the tumors at the onset of therapy, namely mice bearing tumors of >4 mm$^3$ and mice bearing tumors of <4 mm$^3$. Synergistic antitumor efficacy by SN6j plus DOX was detected for these mice bearing the larger tumors (n=4 for each of the four groups) as shown in Table 4.

DETAILED DESCRIPTION OF THE INVENTION

The method of the present invention comprises administration of anti-EDG antibodies in conjunction with administration of chemotherapeutic agents (also referred to herein as anti-tumor agents) wherein the combination has a synergistic anti-tumor effect. The invention should not be construed as limited to use with only the particular anti-EDG antibodies or anti-tumor agents disclosed, but is intended to cover all anti-EDG antibodies and anti-tumor agents. Both monoclonal and polyclonal anti-EDG antibodies may be used. Further, antigen-binding antibody fragments of such antibodies, including F(ab')$_2$, Fab', Fab, Fv, single chain Fv, Fd' and Fd fragments and derivatives of single chain Fv, may be used. These antibodies and/or antibody fragments may be used conjugated or unconjugated. Several anti-EDG antibodies are known in the art and may be used according to the method of the present invention. Known anti-EDG antibodies include K4-2C10 (or termed SN6f), D4-2G10 (or termed SN6a), Y4-2F1 (or termed SN6j) and P3-2G8 (or termed SN6k), SN6, SN6b, SN6c, SN6d, SN6e, SN6g, SN6h and SN6i (10, 15, 16, 25). Further, any anti-tumor agent can be used in this invention. Examples of anti-tumor agents include, but are not limited to, cyclophosphamide (CPA), 5-fluorouracil, paclitaxel, methotrexate, cisplatin and doxorubicin.

Antibodies and anti-tumor agents may be given by a variety of administrative routes, including but not limited to oral, intratumoral, intravenous (i.v.), subcutaneous (s.c.) and intraperitonial (i.p.) methods known to those skilled in the art. The anti-EDG antibodies and the anti-tumor agent(s) may be administered concurrently or sequentially with the administration being repeated as necessary. Suitable concentrations of anti-EDG antibodies are those which induce anti-angiogenesis and anti-tumor effects and for anti-tumor agents are those which are known to have an inhibitory effect on tumor growth. However, as will be shown more fully by the Examples herein, the method of the present invention results in an unexpected synergistic inhibition of tumor growth.

The effectiveness of the method of the present invention has been demonstrated in, for example, a mouse model for the evaluation of chemotherapeutic agents. The use of severe combined immunodeficient (SCID) mice and athymic nude mice with human tumor xenografts has been validated as a model for the evaluation of chemotherapeutic agents, as the model has been shown to reflect the clinical effectiveness of chemotherapeutic agents in original patients treated with these agents. (See for example, Neuwalt et al., 1985, Cancer Res. 45:2827-2833; Ovejera et al., 1978, Annals of Clin. and Lab. Science 8:50).

The method of the present invention is intended to be illustrated by way of the following Examples, which are not meant to be limiting in any way.

EXAMPLE 1

This Example describes the materials and methods used to demonstrate the present invention as further illustrated by the subsequent Examples.

mAbs and Reagents. Anti-human EDG monoclonal antibodies (mAbs) SN6a, SN6f, SN6j and SN6k that cross-react weakly with mouse endothelial cells were used (10, 15, 26). The murine hybridoma cell line Y4-2F1 (producing the monoclonal antibody alternatively termed Y4-2F1 or SN6j) was deposited in American Type Culture Collection ("ATCC") on Aug. 21, 1996, and is designated a ATCC Deposit No. HB-12171. The ATCC is located at 10801 University Boulevard, Manassas, Va., 2010-2209. A non-cross-reactive anti-EDG mAb, SN6h (14, 25), and an isotype-matched murine control IgG (MOPC195 variant, IgG1-κ; ref. 26) were also used. Murine anti-human CD31 mAb JC/70A (IgG1-κ) and cyclophosphamide (CPA) were obtained from DAKO™ (Carpinteria, Calif.) and Sigma™ (St. Louis, Mo.), respectively. Doxorubicin (DOX) was purchased from Sigma™. Rat anti-mouse EDG (CD105) mAb MJ7/18 (rat IgG2a-κ), rat anti-mouse CD31 mAb 390 (rat IgG2a-κ) and an isotype-matched rat control IgG (R35-95; IgG2a-κ) were purchased from PharMingen™ (San Diego, Calif.). InnoGenex™ Mouse-on Mouse Iso-IHC Kit, peroxidase substrate kit DAB (SK-4100), and LSAB Kit Peroxidase Universal (K568) were purchased from InnoGenex™ (San Ramon, Calif.), VECTOR™ (Burlingame, Calif.), and DAKO™, respectively.

Tissues, Cells and Mice. Fresh human neonatal foreskins from elective circumcisions were obtained from the Cooperative Human Tissue Network (CHTN) Eastern Division, University of Pennsylvania Medical Center, and CHTN Pediatric Division, Columbus, Ohio. MCF-7 human breast cancer cells, KM-3 human leukemia cells, human umbilical vein endothelial cells (HUVECs) and SVEC4-10 murine endothelial cells (27) were cultured as described previously (10) and according to methods known to those skilled in the art. Female SCID (NCr) mice were obtained from the Frederick Cancer Research and Developmental Center, National Cancer Institute (Frederick, Md.). Mice were maintained in a protected environment in a laminar flow unit and given sterilized food and water ad libitum as described previously (28) and by methods known to those skilled in the art. All handling of SCID mice was performed in a laminar flow hood.

Antigen-Binding Avidity of mAb. The purified mAbs SN6f, SN6j and SN6k were individually radiolabeled with $^{125}$I using Iodo-Gen and according to standard methods known to those skilled in the art (for example, see Reference 16). The radiolabeled SN6f, SN6j and SN6k were determined to contain 1.85, 0.73 and 1.29 iodine atoms per IgG molecule on the average, respectively. Titration experiments which were carried out using a fixed amount (0.1 μg) of each $^{125}$I-labeled mAb and 2-fold serial increments of EDG-expressing KM-3 cells showed that 48.6, 50.0 and 55.0%, respectively, of the labeled SN6f, SN6j and SN6k retained antigen-binding activity. In the analyses of the binding data for SN6f, SN6j and SN6k, corrections were made for the above numbers. Analysis of Scatchard plot of binding data was carried out as described previously (29, 30). An equilibrium constant and an average maximal number of mAb bound/cell were estimated by this analysis.

Cellular Radioimmunoassay (RIA). An indirect cellular RIA was used to determine the reactivities of anti-human EDG mAbs with murine endothelial cells. Details of the assay were described previously (31) and were carried out using procedures known to those skilled in the art. Briefly, mAbs and an isotype-matched control IgG were individually incubated, in triplicate, with target cells in wells of 96-well microtiter plates at 4° C. for varying periods of time. After the cells were pelleted and washed three times, $^{125}$I-labeled F(ab')$_2$ of affinity-purified goat anti-mouse IgG antibodies was added to the cells and the reaction mixtures were incubated at 4° C. for 1 h. After the cells were washed four times, the radioactivity in the washed cells was determined (Cobra™ Series Autogamma Counter; Packard Instrument Comp.™, Meriden, Conn.).

Chimeric Human/Mouse Model. Fresh human neonatal foreskins were stored in sterile RPMI 1640 media supplemented with 2% fetal bovine serum, 1% gentamycin and 2.5 μg/ml fungizone. The tissues were used for grafting on the same day as received. The grafting into SCID mice was performed by standard method (32-34) with slight modifications.

Female SCID mice (7-10 week old) were anesthetized and a section of skin (approximately 2 cm$^2$) is surgically removed. A precut section of fresh full thickness human neonatal foreskin is sutured into place. The grafts are bandaged securely for 2 weeks to allow healing. EDG-negative MCF-7 cells are inoculated intradermally (i.d.) into the grafted human skins over 7 weeks after the skins were grafted and the graft healed completely.

Immunostaining of Tissues. Serial sections (6 μm thickness) were cut from the frozen tissues using a cryostat, fixed in cold acetone, and stored at −70° C. until use. Human and mouse blood vessels in the tissue slice were determined by immunohistochemical staining using species-specific anti-endothelial mAbs, i.e., mouse anti-human EDG mAb (SN6h), mouse anti-human CD31 mAb, rat anti-mouse EDG (CD105) mAb, and rat anti-mouse CD31 mAb. In the immunostaining, isotype-matched control murine IgG (MOPC 195 variant; IgG1-κ) and isotype-matched control rat IgG (R35-95; IgG2a-κ) were included as controls. For immunostaining of mouse tissues using mouse mAbs, InnoGenex™ Mouse-on Mouse Iso-IHC Kit and VECTOR peroxidase substrate kit DAB were used following the manufacturer's instructions to reduce background staining. For immunostaining of mouse tissues using rat mAbs, DAKO LSAB Kit Peroxidase Universal™ was used. Counterstaining was performed with hematoxylin. The ratio of human vessels to mouse vessels in the completely healed human skin grafts (i.e., 8 weeks after the grafting) and in the human skin grafts bearing MCF-7 tumors was determined by counting human and mouse vessels on four 100× fields (i.e., 10× objective lens and 10× ocular lens) at the area of highest vascularization (35) in each tissue section under a microscope. Serial sections of the human skins were stained with SN6h, anti-human CD31 mAb, anti-mouse CD105 mAb, and anti-mouse CD31 mAb. In addition, the tissues were stained with a mixture of SN6h and anti-human CD31 mAb, and a mixture of anti-mouse CD105 mAb and anti-mouse CD31 mAb.

In addition, mouse and human vessels were immunostained in the tumors from the chimera mice that received PBS (control), SN6j, CPA or SN6j plus CPA, and were sacrificed at the end of a therapeutic experiment. Large tumors of two different sizes (i.e., 350-450 mm$^3$ and 100-250 mm$^3$) were obtained from each group of mice for immunostaining and vessel counting. Sections of the tumors were stained with individual mAbs or a mixture of anti-human CD105 and CD31 mAbs and a mixture of anti-mouse CD105 and CD31 mAbs as described above. Human and mouse vessels were counted separately as described above. An average of vessel counts in the two tumors was compared between different groups.

Antiangiogenic Therapy of Preformed Human Tumors in Human Skins Grafted into SCID Mice. MCF-7 cells (8×10$^6$ cells in 0.1 ml PBS) were transplanted i.d. into human full-thickness skins grafted into SCID mice when the grafts showed no signs of inflammation, contraction or rejection. The mice were left untreated until distinct palpable tumors (3 to 6 mm in diameter in most cases) appeared. Mice with distinct tumors were divided into groups for the therapeutic studies. Anti-EDG mAbs and an isotype-matched control IgG (MOPC 195 variant; IgG1-κ) were centrifuged at 100,000 g and 4° C. for 1 hr and the supernates were individually filtered through a sterile Millex-GV™ filter (0.22 µm; Millipore™, Bedford, Mass.) in a laminar flow hood before use. The sterilized solutions were diluted with sterile PBS containing mouse serum albumin (0.05% final concentration). For the mAb therapy, 200 µg/0.2 ml mAb or control IgG was administered i.v. via the tail vein of mice. The administration was repeated four times every two days in the experiments of FIGS. 3, 4 and 5, but every three days in the experiments of FIGS. 6 and 7. The second cycle of the mAb therapy in FIGS. 6 and 7 was performed by injecting every four days for the five injections. For the combination therapy with CPA, 200 µg mAb and CPA (80 mg/kg body weight) were given i.v. and i.p., respectively. CPA was given following an antiangiogenic schedule (36, 37). Administration of the mAb and CPA was repeated as indicated in FIGS. 6 and 7. Three control groups received PBS, mAb and CPA, respectively.

In an additional study, therapy of established tumors of MCF-7 in human skin/SCID mouse chimeras was performed using DOX, SN6j or SN6j plus DOX. MCF-7 tumor was generated as described above. Two sets of experiments were carried out in this study. In the first set of experiments, mice with distinct tumors were distributed into four groups for the therapeutic study. The tumor-bearing mice were treated by administration of 1) an isotype-matched control IgG (MOPC 195 variant; IgG1-κ) plus saline (control of DOX), 2) SN6j plus saline, 3) control IgG plus DOX, or 4) SN6j plus DOX. For the mAb therapy, 100 µg/0.2 ml PBS of SN6j or control IgG was given i.v. per 25 g body weight of mice. For the drug therapy, 25 µg DOX in 25 µl saline or 25 µl saline (control) was given i.p. per 25 g body weight of mice. The injections of the mAb and/or drug were repeated five times at 3-day intervals as shown in FIG. 8.

The second set of the therapeutic experiment was performed as described above. The results are shown in FIG. 9. The results of the two sets of experiments shown in FIG. 8 and FIG. 9 are consistent with each other and demonstrate a synergistic effect on tumor volume reduction when SN6j and DOX are administered together.

Follow-up of Treatment Efficacy. During the treatment, mice were monitored daily for tumor size and morbidity. Mice were weighed twice a week using an electronic balance (OHAUS™ Model GT210). Tumor size was measured twice or three times a week using an electronic caliper (PRO-MAX 6 inch caliper; Fowler Co., Newton, Mass.) that was connected to a computer using OptoDemo™ software (Fowler Co.). The measured tumor diameters were converted to tumor volumes using Excel 97™; the tumor volumes were calculated using the following formula (38): V=length×width×height×π/6. Statistical analysis of the data for the comparison of different groups of mice was carried out using Student's t-test.

EXAMPLE 2

Immunostaining of Blood Vessels in Tissues from Human Skin/SCID Mouse Chimeras. Vessels in the human skin grafts generated as described in Example 1 above and the adjacent mouse tissues were analyzed by immunohistochemical staining with species-specific anti-endothelial mAbs, i.e., SN6h (an anti-human CD105 mAb), anti-human CD31 mAb, anti-mouse CD105 mAb and anti-mouse CD31 mAb. The ratio of human vessels to mouse vessels in the completely healed human skin grafts and in the skin grafts bearing large MCF-7 tumors was determined in serial sections of the tissues by counting human vessels and mouse vessels. Human vessels were detected by immunostaining the tissue sections with a mixture of SN6h and anti-human CD31 mAb, whereas mouse vessels were detected by immunostaining with a mixture of anti-mouse CD105 mAb and anti-mouse CD31 mAb. Blood vessels in the completely healed (8 weeks after grafting) human skin without tumors consisted of 43.5% human vessels and 56.5% mouse vessels. Blood vessels in the human skin bearing a large established human tumor (250 mm$^3$) consisted of 59.6% human vessels and 40.4% mouse vessels. Therefore, growth of tumors in the human skin grafts depended on both murine and human vessels. The results also indicate that human tumors stimulate human vessels preferentially compared with murine vessels. Immunostaining of vessels was also performed using individual mAbs.

Figure 1:
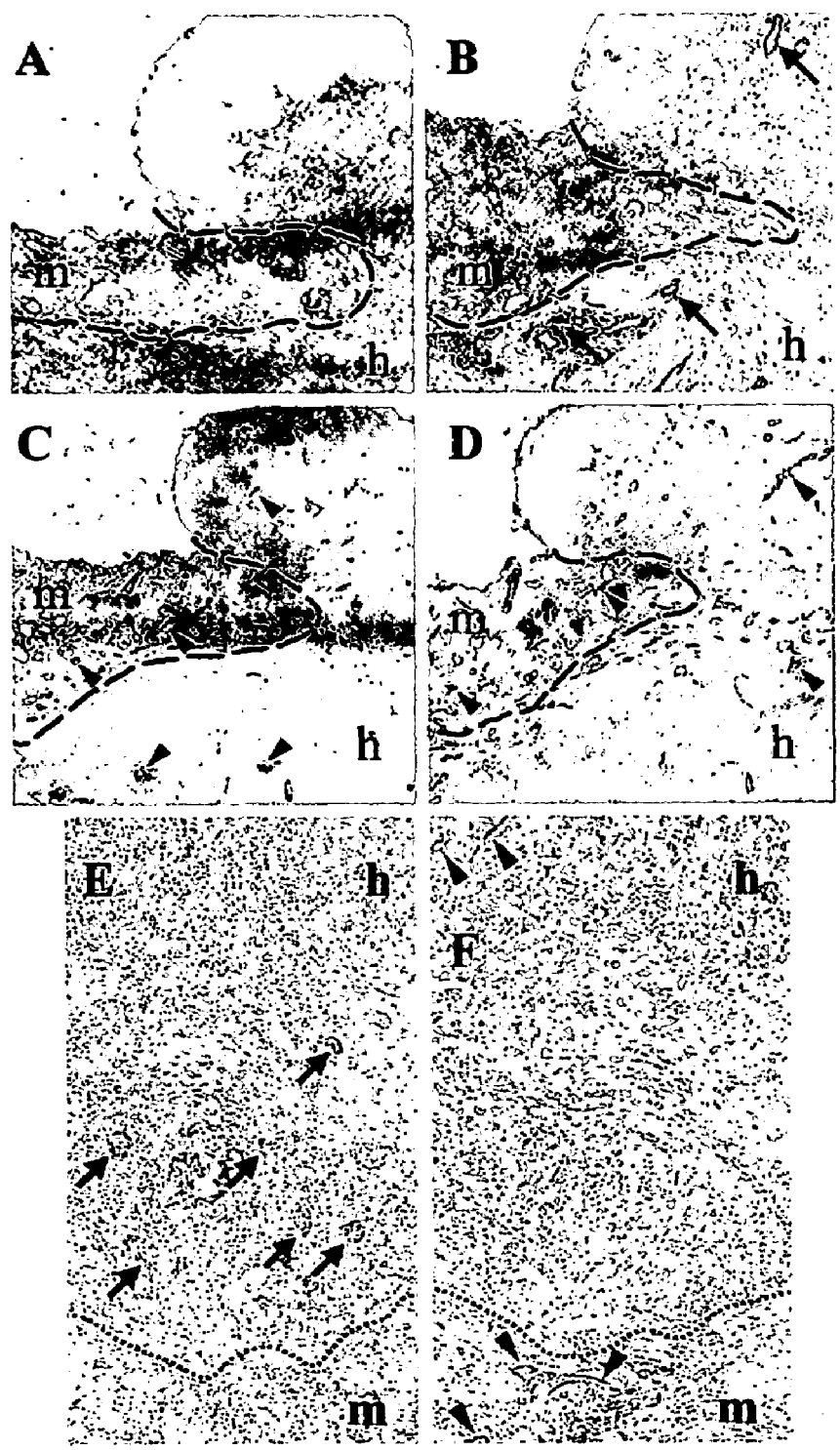
FIG. 1. Immunostaining of blood vessels in the human skin/SCID mouse chimeras using species-specific anti-EDG (CD105) and anti-CD31 mAbs. Serial sections were cut from frozen tissues containing the human-mouse skins junction region (panel A-panel D, X100). Tissue sections were immunostained with SN6h (an anti-human CD105 mAb; A), anti-human CD31 mAb (panel B), anti-mouse CD105 mAb (panel C) and anti-mouse CD31 mAb (panel D). In an additional study, serial sections were cut from frozen tissues of the grafted human skins bearing large (250 mm$^3$) MCF-7 human tumors (E and F, X200). SN6h stained multiple vessels in the tumor in the human skin but not in the adjacent murine subcutaneous tissue (E). Anti-mouse CD105 mAb stained multiple vessels in the tumor in the human skin and the murine subcutaneous tissue (F). A few examples of stained human and mouse vessels are indicated by arrows (E) and arrow heads (F), respectively.

The stained vessels in the human skin grafts and adjacent mouse skins are illustrated in FIG. 1 panels A-D. In addition, vessels in MCF-7 tumors in the grafted human skins and the adjacent subcutaneous murine tissues are illustrated in FIG. 1 panels E and F. SN6h did not stain any vessels in the grafted human skins or adjacent mouse skins (FIG. 1 panel A). However, SN6h stained multiple vessels in tumors in the human skins but not in the adjacent murine subcutaneous tissues (FIG. 1 panel E). The results show that SN6h is capable of distinguishing the tumor-induced angiogenic vessels from the non-angiogenic vessels. In contrast, anti-human CD31 mAb stained vessels in the tumor-free human skins (FIG. 1 panel B) and also vessels in the tumors in the grafted human skins (data not shown). It did not stain any vessels in the adjacent murine skins (FIG. 1 panel B). Anti-mouse CD105 mAb stained vessels in the human skins as well as in the adjacent murine skins (FIG. 1 panel C). It also stained vessels in MCF-7 tumors in the human skins and vessels in the adjacent murine subcutaneous tissues (FIG. 1 panel F).

Thus, unlike SN6h, the anti-mouse CD105 mAb was unable to distinguish the non-angiogenic vessels from the tumor-induced angiogenic vessels. The staining pattern of anti-mouse CD31 mAb is similar to that of anti-mouse CD105 mAb; the former stained vessels in the human skins as well as in the adjacent murine skins (FIG. 1 panel D). The described immunostaining pattern of human skin grafts and the adjacent mouse tissues was consistently observed for the tissue samples obtained 7, 8, 9, 11, 18 and 20 weeks after grafting of the human skins. Specificity of the anti-mouse CD105 and anti-mouse CD31 mAbs for murine vessels was confirmed by immunohistochemical studies in which these mAbs did not react with any blood vessels in human colon cancer tissues and human neonatal foreskins. The results show that the growth of human vessels is limited within the boundary of the grafted human skins, but murine vessels infiltrate into the grafted human skins from the surrounding murine tissues. Therefore, murine vessels are more functional for delivering nutrients and oxygen than human vessels in the human skin grafts.

EXAMPLE 3

Antibody Avidity and Number of Available Epitopes on EDG-Expressing Cells. Scatchard plot analyses of direct binding of radiolabeled SN6f, SN6j and SN6k to EDG-expressing KM-3 leukemia cells and subconfluent proliferating HUVECs were carried out (FIG. 2). The results show equilibrium constants of $8.02 \times 10^9$, $2.85 \times 10^9$, and $1.01 \times 10^9$ liters/mol, respectively, for SN6f, SN6j and SN6k to KM-3 cells. The equilibrium constants to HUVECs are $8.32 \times 10^9$, $3.08 \times 10^9$, and $1.01 \times 10^9$, respectively, for SN6f, SN6j and SN6k.

The results show that these mAbs bind to KM-3 cells and HUVECs with very similar avidities. The three mAbs all show good binding avidities and the rank order of these mAbs for antibody avidity is SN6f>SN6j>SN6k. In the same analyses of Scatchard plot, the average number of antibody molecules bound per KM-3 cell was estimated to be $1.25 \times 10^4$, $1.75 \times 10^4$ and $1.70 \times 10^4$, respectively, at antibody saturation. The number per HUVEC was estimated to be $1.56 \times 10^6$, $1.13 \times^9 10^6$ and $1.52 \times 10^6$, respectively, for SN6f, SN6j and SN6k. Since these mAbs (all IgG1) are bivalent antibodies, the average number of antigen on these cell specimens is likely to be 1 to 2-fold greater than the antibody number. The present results show that EDG is highly expressed on proliferating HUVECs and they express approximately one-hundred fold as many EDG molecules as KM-3 cells.

EXAMPLE 4

Reactivities of Anti-EDG mAbs with Murine Endothelial Cells. An indirect cellular RIA was used to determine the reactivities of SN6f, SN6j and SN6k with proliferating (subconfluent) SVEC4-10 murine endothelial cells by incubation for 2 h or 24 h. The radioactivities (cpm) in the cells treated with SN6f, SN6j, SN6k and an isotype-matched control IgG (IgG1-κ) for 2 h were 414±46 (S.D.), 381±15, 394±36 and 290±29, respectively. The radioactivities in the cells treated with the mAbs and control IgG for 24 h were 926±32, 758±64, 662±30 and 456±60, respectively. In the same assay, the radioactivities in proliferating HUVECs treated with SN6f and control IgG for 2 h were 8,227±385 and 196±24, respectively. The results show that binding of the three anti-EDG mAbs to SVEC4-10 murine endothelial cells is weak but significant compared with the isotype-matched control IgG. The rank order of the three mAbs for reactivity with SVEC4-10 cells is SN6f>SN6j~SN6k. The reactivities of these mAbs with HUVECs are much stronger than those with SVEC4-10 murine endothelial cells (see above and ref. 15).

EXAMPLE 5

Suppression of Established Tumors by Systemic Administration of Naked (unconjugated) mAbs. MCF-7 human breast cancer cells ($8 \times 10^6$ cells/mouse) were injected i.d. into human skins grafted to SCID mice, and left untreated until distinct palpable tumors appeared. Mice with distinct tumors were divided into groups (n=6 or 5; [n=6 except for PBS (n=5) and MOPC (n=5) groups]), and treated by i.v. administration of PBS, an isotype-matched control IgG (MOPC 195 variant; IgG1-κ), SN6f, SN6j, SN6k or SN6f plus SN6k. SN6f and SN6k define mutually distant epitopes (15). The therapy was performed in two cycles including one-week pause between the cycles to relieve the mice from the i.v. injection-associated stress. Each cycle consisted of five injections, at 2-days intervals, of PBS, a control IgG (200 µg), a mAb (200 µg) or a mixture of SN6f (200 µg) and SN6k (200 µg) as indicated in the figure. The results are presented in FIG. 3. Both SN6j and SN6k showed significant anti-tumor efficacy while SN6f was less effective. The results indicate that anti-tumor efficacy of anti-EDG mAbs is not directly proportional to antigen-binding avidities of mAbs because SN6f shows the strongest antigen-binding avidity among the three mAbs to both HUVECs and murine endothelial cells (see above).

The observed difference in the anti-tumor efficacy among SN6f, SN6j and SN6k is consistent with the difference among the deglycosylated ricin A chain (dgRA) conjugates of the three mAbs (15). The results suggest the importance of other factors such as epitopes in the in vivo anti-tumor efficacy. The combination of SN6f and SN6k showed an additive effect.

In additional tests, effect of the mAb dose on the anti-tumor efficacy was investigated. An example of such tests is presented in FIG. 4. A two-fold increase of SN6k from 200 µg to 400 µg resulted in a small increase in the anti-tumor efficacy. Both 200 µg and 400 µg of SN6k were effective for tumor suppression compared with 400 µg of an isotype-matched control IgG. A similar test was performed with SN6j (FIG. 5). Both 200 µg and 400 µg of SN6j were effective for tumor suppression compared with the isotype-matched control IgG. The difference in the anti-tumor efficacy between 200 µg and 400 µg of SN6j was small. The results show that naked anti-EDG mAbs can suppress growth of established tumors.

EXAMPLE 6

Synergistic Anti-tumor Efficacy by Combination of a mAb with a Chemotherapeutic Drug. To improve anti-tumor efficacy of the naked anti-EDG mAb, SN6j was combined with CPA which was administered into tumor-bearing chimeras using an antiangiogenic schedule of drug dosing (36, 37) or in another term, a metronomic dosing regimen (39) A conventional dosing schedule of a cytotoxic drug for cancer therapy consists of application of the drug at or near the maximum tolerated dose, followed by periods of rest of the drug dosing to allow normal tissues of the patients to recover. In the antiangiogenic schedule of drug dosing (or in another term, a metronomic drug dosing schedule), a relatively low dose of a cytotoxic drug is given continuously or at shorter intervals without interruption (36, 37, 39). MCF-7 tumors in human skin grafts in SCID mice were established as described in Example 1 above.

Chimeras with established tumors were distributed into four groups (n=8). Individual groups were treated by systemic administration of PBS, SN6j, CPA, or SN6j plus CPA. CPA (80 mg/kg body weight) was injected i.p. every 4 days by using an antiangiogenic schedule (see above). SN6j (200 µg) was administered i.v. every 3 days for the first 5 injections and every 4 days for the remaining 5 injections. The results are presented in FIG. 6. It should be noted that at the onset of therapy, the average size of tumors in the present set of experiments is larger than those presented in FIGS. 3, 4 and 5; the average size of tumors was 63.8, 57.5, 54.6 and 97.2 mm$^3$, respectively, for FIGS. 3, 4, 5 and 6. Both SN6j and CPA are effective for tumor suppression. Difference in the tumor size between the control PBS group and the SN6j/CPA-treated group is statistically significant (p<0.04) after day 45 and until the end of experiment, i.e., day 66. The statistically significant experimental points are indicated by star symbols.

Potential synergy between SN6j and CPA was evaluated by methods known to those skilled in the art, such as the method detailed for detecting synergy between angiostatin and endostatin (40) and synergy between an adenovirus variant and docetaxel (41). Previously, Momparler (42) reviewed in vitro systems for evaluation of combination chemotherapy of malignant diseases. In this review article, Momparler described quantitative parameters for synergistic, additive and subadditive effects between two drugs on the drug-induced cell lethality (42). Recently, Yokoyama et al. (40) and Yu et al. (41) applied this principle to the combination therapy of tumors in vivo. Yokoyama et al. (40) treated athymic nude mice bearing human ovarian tumors with angiostatin and endostatin while Yu et al. (41) treated nude mice bearing human prostate tumors with CV787, a prostate-specific antigen (PSA)-positive prostate cell-specific adenovirus variant, and docetaxel. They analyzed anti-tumor efficacy of the combination therapy using the same method that is based on the Momparler's description (42). Details of the analysis are described by both Yokoyama et al. (40) and Yu et al. (41). We used the same method for analyzing combination effects of SN6j and a drug (CPA or DOX) on MCF-7 human breast tumors in human skin/SCID mouse chimeras. Details of the analytical method are described in Table 1 and Table 2. Table 1 summarizes relative tumor volume of treated groups versus control group on five different time points during the therapy. Combination therapy showed more than additive effect on tumor growth suppression. On day 24, 9 days after therapy initiation, there was a slight improvement in anti-tumor activity in the combination group when compared with the expected additive effect. This improvement became greater during the course of therapy. On days 34 and 45, there were 1.5-fold and 1.6-fold improvements, respectively, in the combination group compared with the expected additive effect (Table 1).

TABLE 1

Combination therapy with SN6j and CPA

Fractional tumor volume (FTV)$^b$ relative to untreated controls

| Day$^a$ | SN6j | CPA | Expected$^c$ | Observed | Ratio of expected:observed FTV$^d$ |
|---|---|---|---|---|---|
| 24 | 0.824 | 0.867 | 0.714 | 0.651 | 1.097 |
| 34 | 0.962 | 0.873 | 0.840 | 0.555 | 1.514 |
| 45 | 0.929 | 0.827 | 0.768 | 0.474 | 1.620 |
| 55 | 0.763 | 0.702 | 0.536 | 0.435 | 1.232 |
| 66 | 0.743 | 0.739 | 0.549 | 0.426 | 1.289 |

$^a$Day after tumor cell inoculation. Tumor volume was measured twice or three times a week for each mouse (n = 8 for each group of mice).
$^b$FTV, calculated as mean tumor volume experimental/mean tumor volume control.
$^c$(Mean FTV of SN6j) × (mean FTV of CPA)
$^d$Obtained by dividing the expected FTV by the observed FTV. A ratio of >1 indicates a synergistic effect, and a ratio of <1 indicates a less than additive effect. This supraadditive effect of the combination therapy persisted until the end of experiment (i.e., day 66).

The results demonstrate a synergistic anti-tumor effect of an anti-EDG antibody and an anti-tumor agent, as SN6j and CPA exert synergistic anti-tumor efficacy in the present model. Small decreases in the body weight were observed for the chimeras treated with CPA and CPA plus SN6j; the decreases were within 10% of the control. Therapeutic effect on individual chimeras in each group of FIG. 6 is presented in FIG. 7. Growth rate of MCF-7 tumors in the human skin/SCID mouse chimeras is substantially heterogeneous before onset of the therapy. This is in contrast to more homogeneous growth of the MCF-7 tumors in SCID mice (e.g., ref. 15). One reason for this heterogeneous growth in the chimeras may be the wider genetic heterogeneity of the human skins compared with SCID mice. To minimize the effect of the heterogeneous tumor size on the experiment, chimeras with tumors of a similar size were distributed nearly evenly into different groups. Consequently, the average size of tumors in each group became similar among the four groups at the onset of therapy (see FIG. 6). Tumors in 8 chimeras of the control PBS group all continued growing although growth rate of one tumor was substantially slower than others (FIG. 7 panel A). Treatment with SN6j slowed tumor growth compared with the control group and a small tumor in one chimera regressed completely (FIG. 7 panel B). CPA therapy using an antiangiogenic schedule slowed growth of five smaller established tumors and induced near regression of one of the tumors. However, CPA therapy showed little therapeutic effect on the three large tumors of more than 100 mm$^3$ at the onset of therapy (FIG. 7 panel C). Treatment with SN6j and CPA using an antiangiogenic schedule of drug dosing prevented five smaller established tumors from increasing in size and induced lasting complete regression of two of the tumors (FIG. 7 panel D). An additional tumor regressed after day 37 but relapsed soon after the regression. The combination therapy prevented one of the three large tumors of more than 100 mm$^3$ from increasing in size soon after the initiation of therapy and the tumor remained stable during and after the therapy (FIG. 7 panel D). Two of the large tumors continued growing initially but became stable after 3 injections of SN6j and CPA; these tumors restarted expanding after cessation of therapy. Thus, the present Example demonstrates that the combination of SN6j and CPA is effective for treating both small and large established tumors.

Human and murine blood vessels were immunostained in the large human tumors from the chimera mice after the mice were sacrificed at the end of experiment shown in FIG. 7. Number of murine vessels in the tumors was 52, 47, 47 and 34 per 100× field for groups A, B, C and D, respectively (see FIG. 7 for the groups). Therefore, SN6j (group B) and CPA (group C) caused only a small decrease (approximately 10%) in the number of murine vessels in the tumors compared with the control (group A). However, combination of SN6j and CPA (group D) caused a larger (i.e., 35%) decrease in the number of murine vessels. Number of human vessels in the tumors was 33, 0, 36 and 0 per 100× field for groups A, B, C and D. The results show that SN6j is highly effective for suppressing human vessels but only weakly suppressive against murine vessels. CPA was not effective for inhibiting human vessels and only weakly suppressive against murine vessels. However, a combination of SN6j and CPA showed a stronger suppression of murine vessels and was effective in eliminating human vessels in the tumors. Further, no strong toxicity was observed by the combination therapy although transient decreases in the body weight (<10%) of the chimeras were detected.

In an additional study, SN6j was combined with DOX which was administered into tumor-bearing human skin/SCID mouse chimeras using an antiangiogenic schedule of drug dosing (see above). MCF-7 tumor in the chimeras was established as described above. Chimeras with established tumors were distributed into four groups (n=7 except for the control IgG plus saline group for which n=6). Individual groups were treated by systemic administration of an isotype-matched control IgG (MOPC 195 variant; IgG1-κ) plus saline (control of DOX), the control IgG plus DOX, SN6j plus saline, or SN6j plus DOX. DOX (25 µg in 25 µl saline/25 g body weight of mice) and saline (25 µl/25 g body weight) were injected i.p. at 3-days intervals for a total of six injections. SN6j (100 µg in 0.2 ml PBS/25 g body weight) and the control IgG (ibid) were administered i.v. at 3-days interval for a total of six injections. The results are presented in FIG. 8.

Potential synergy between SN6j and DOX was evaluated by the method described for Table 1. Results are shown in Table 2 which summarizes relative tumor volume of treated groups versus control group on five different time points during the therapy. Combination therapy using SN6j and DOX showed more than additive effect on tumor growth suppression. On day 21, there was a slight improvement in anti-tumor activity in the combination group when compared with the expected additive effect. This improvement became greater during the course of therapy. On days 29 and 33, there were 1.36-fold and 1.30-fold improvements, respectively, in the combination group compared with the expected additive effect (Table 2).

TABLE 2

Combination Therapy with SN6j and DOX

Fractional Tumor Volume (FTV)[b] Relative to MOPC + Saline Group

| Day[a] | SN6j | Dox | Combination Treatment Expected[c] | Observed | Ratio of Expected:Observed FTV[d] |
|---|---|---|---|---|---|
| 21.0 | 0.855 | 0.993 | 0.849 | 0.780 | 1.088 |
| 26.0 | 0.917 | 0.967 | 0.886 | 0.688 | 1.288 |
| 29.0 | 0.913 | 0.980 | 0.895 | 0.658 | 1.361 |
| 33.0 | 0.852 | 0.900 | 0.767 | 0.587 | 1.306 |
| 36.0 | 0.846 | 0.856 | 0.724 | 0.571 | 1.269 |

[a]Days after tumor cell inoculation. Tumor volume was measured twice or three times a week for each mouse (n = 7 for ach group of mice except for the MOPC plus saline control group for which n = 6).
[b]FTV, calculated as mean tumor volume treatment/mean tumor volume control, i.e., MOPC plus Saline group.
[c](Mean FTV of SN6j) × (Mean FTV of Dox).
[d]Obtained by dividing the expected FTV by the observed FTV. A ratio of >1 indicares a synergistic effect, and a ratio of <1 indicates a less than additive effect.

This supraadditive effect of the combination therapy persisted until the end of experiment (i.e., day 36).

The combination therapy of established tumors using SN6j and DOX was repeated and the results are shown in FIG. 9. The results of FIG. 9 are consistent with the results of the first experiment shown in FIG. 8. These results show that SN6j and DOX exert synergistic anti-tumor efficacy against established tumors.

Collectively, the presented results demonstrate synergistic anti-tumor effect of an anti-EDG antibody and an anti-tumor agent as SN6j and CPA as well as SN6j and DOX exert synergistic anti-tumor efficacy in the present model.

EXAMPLE 7

Examples 7-9 describe the materials and methods used to demonstrate another embodiment of the present invention.

mAbs and Reagents. Anti-human EDG monoclonal antibody (mAb) SN6j that cross-react weakly with mouse endothelial cells was used (15, 25). An isotype-matched murine control IgG (MOPC195 variant, IgG1-k; ref. 10) was also used. Doxorubicin (DOX) was purchased from Sigma™.

Cells and Mice. Colon-26 murine colon carcinoma cell line was kindly provided by Dr. Tateshi Kataoka (Cancer Chemotherapy Center, Tokyo, Japan) and cultured in a monolayer in RPMI 1640 media containing 10% fetal bovine serum (FBS), 100 unit/ml penicillin, 100 µg/ml streptomycin, and 250 ng/ml amphotericin B. SVEC4-10 murine endothelial cells were cultured as described previously (10) and according to methods known to those skilled in the art. KM-3 and MOLT-4 human leukemia cell lines were cultured as described before (10). All cells were cultured in a humidified atmosphere with 5% $CO_2$ at 37° C.

Five to six-week-old BALB/c mice were obtained from National Cancer Institute (Bethesda, Md.). They were used for experiments after being acclimated for at least a week. They were supplied autoclaved food and water ad libitum as described previously (10) and by methods known to those skilled in the art. All handling of the mice was performed in a laminar flow hood.

Cellular Radioimmunoassay (RIA). An indirect cellular RIA was used to determine the reactivity of anti-human EDG mAb SN6j with SVEC4-10 murine endothelial cells, colon-26 murine colon carcinoma cells and control cells (KM-3 human B-lineage leukemia cells and MOLT-4 human T-lineage leukemia cells). Details of the assay were described previously (26) and were carried out using procedures known to those skilled in the art. Briefly, mAbs and an isotype-matched control IgG were individually incubated, in triplicate, with target cells in wells of 96-well microtiter plates at 4° C. for varying periods of time. After the cells were pelleted and washed three times, $^{125}$I-labeled F(ab')$_2$ of affinity-purified goat anti-mouse IgG antibodies was added to the cells and the reaction mixtures were incubated at 4° C. for 1 h. After the cells were washed four times, the radioactivity in the washed cells was determined (Cobra™ Series Auto-gamma Counter; Packard Instrument Comp.™, Meriden, Conn.).

Antiangiogenic Therapy of Preformed Colon Tumors in Mice. Colon-26 cells ($1.25 \times 10^5$ cells in 0.1 ml PBS) were inoculated subcutaneously (s.c.) into left flank of BALB/c mice. The mice were left untreated until distinct palpable tumors appeared. Mice with distinct and typical s.c. tumors were divided into groups for the therapeutic studies. Anti-EDG mAb SN6j and an isotype-matched control IgG (MOPC 195 variant; IgG1-κ) were centrifuged at 100,000 g and 4° C. for 1 hr and the supernates were individually filtered through a sterile Millex-GV™ filter (0.22 µm; Millipore™, Bedford, Mass.) in a laminar flow hood before use. The sterilized solutions were diluted with sterile PBS containing mouse serum albumin (0.05% final concentration). For the mAb therapy, 1.8 µg/g body weight of SN6j or control IgG was administered i.v. via the tail vein of mice. Doxorubicin (0.5 µg/g body weight) was injected intraperitoneally (i.p.) into mice. The administration was repeated three times at 4 days intervals.

Follow-up of Treatment Efficacy. During the treatment, mice were monitored daily for tumor size and morbidity. Mice were weighed twice a week using an electronic balance (OHAUS™ Model GT210). Tumor size was measured twice or three times a week using an electronic caliper (PRO-MAX 6 inch caliper; Fowler Co., Newton, Mass.) that was connected to a computer using OptoDemo™ software (Fowler Co.). The measured tumor diameters were converted to tumor volumes using Excel 97™; the tumor volumes were calculated using the following formula (27): V=length×width×height×π/6.

EXAMPLE 8

Reactivity of Anti-EDG mAb SN6j with Murine Endothelial Cells and Murine Colon Cancer Cells. An indirect cellular RIA was used to determine the reactivity of SN6j with proliferating (subconfluent) SVEC4-10 murine endothelial cells by incubation for 2 h or 24 h. The radioactivities (cpm) in the cells treated with SN6j and an isotype-matched control IgG (IgG1-κ) for 2 h were 381±15 (S.D.) and 290±29, respectively. The radioactivities in the cells treated with SN6j and control IgG for 24 h were 758±64 (S.D.) and 456±60, respectively. The reactivity of SN6j with SVEC4-10 cells was confirmed by flow cytometry analysis (15). The results show that binding of SN6j to SVEC4-10 murine endothelial cells is weak but significant compared with the isotype-matched control IgG. The reactivity of SN6j with proliferating human umbilical vein endothelial cells (HUVECs) are much stronger than those with SVEC4-10 murine endothelial cells (15).

Potential reactivity of SN6j with colon-26 cells was tested by a cellular RIA (26). In the assay, EDG-positive KM-3 human B-lineage leukemia cells and EDG-negative MOLT-4 human T leukemia cells (16) were included as a positive and a negative control, respectively. In addition, an isotype-matched control IgG was included as another negative control. The binding value of SN6j to colon-26 (140±24 cpm) was similar to that of SN6j to MOLT-4 (161±50 cpm) while the value was much lower than that of SN6j to KM-3 (1,464±151 cpm). The binding values of the control IgG to colon-26, KM-3 and MOLT-4 were similar, i.e., 185±40 cpm, 177±45 cpm and 139±22 cpm, respectively. The results indicate that the observed binding value (140±24 cpm) of SN6j to colon-26 represents a background value of the assay and SN6j does not react with colon-26 cells.

EXAMPLE 9

Synergistic Anti-tumor Efficacy by Combination of a anti-EDG mAb with a Chemotherapeutic Drug. To improve anti-tumor efficacy of the naked anti-EDG mAb, SN6j was combined with doxorubicin (DOX) which was administered into tumor-bearing mice using an antiangiogenic schedule of drug dosing (28, 29) or in another term, a metronomic dosing regimen (30) A conventional dosing schedule of a cytotoxic drug for cancer therapy consists of application of the drug at or near the maximum tolerated dose, followed by periods of rest of the drug dosing to allow normal tissues of the patients to recover. In the antiangiogenic schedule of drug dosing (or in another term, a metronomic drug dosing schedule), a relatively low dose of a cytotoxic drug is given continuously or at shorter intervals without interruption (28, 29, 30). Colon-26 tumors in BALB/c mice were established as described in Example 7 above.

Mice with established typical s.c. tumors were distributed into four groups (n=8 except for DOX group for which n=9). Individual groups were treated by systemic administration of an isotype-matched control IgG (MOPC195v), SN6j, DOX, or SN6j plus DOX. SN6j (1.8 µg/g body weight) and MOPC195v (1.8 µg/g body weight) were injected i.v. while DOX (0.5 µg/g body weight) was injected i.p. The injectections were repeated three times at 4 days intervals. The test results are shown in FIG. 10 and FIG. 11.

Potential synergy between SN6j and DOX was evaluated by methods known to those skilled in the art, such as the method detailed for detecting synergy between angiostatin and endostatin (31), synergy between an adenovirus variant and docetaxel (32) and SN6j and CPA (25). Previously, Momparler (33) reviewed in vitro systems for evaluation of combination chemotherapy of malignant diseases. In this review article, Momparler described quantitative parameters for synergistic, additive and subadditive effects between two drugs on the drug-induced cell lethality (33). Recently, Yokoyama et al. (31), Yu et al. (32) and my group (25) applied this principle to the combination therapy of tumors in vivo. Yokoyama et al. (31) treated athymic nude mice bearing human ovarian tumors with angiostatin and endostatin, Yu et al. (32) treated nude mice bearing human prostate tumors with CV787, a prostate-specific antigen (PSA)-positive prostate cell-specific adenovirus variant, and docetaxel, and we treated human skin/SCID mouse chimeras bearing human breast tumors with SN6j and CPA (25). These researchers including us analyzed anti-tumor efficacy of the combination therapy using the same method that is based on the Momparler's description (33). Details of the analysis were described by Yokoyama et al. (31), Yu et al. (32) and us (25). In the present analysis, we used the same method for analyzing combination effects of SN6j and a drug (DOX) on colon-26 colon tumors in mice. Details of the analytical method are described in Table 3. This table summarizes relative tumor volume of treated groups versus control group on eight different time points during the therapy. Combination therapy showed more than additive effect on tumor growth suppression on days 15, 17 and 19. On day 15, 11 days after therapy initiation, there was a slight improvement in anti-tumor activity in the combination group when compared with the expected additive effect. This improvement persisted until the end of the therapy experiment (Table 3).

TABLE 3

Combination Therapy of Colon-26 Tumors with SN6j and Doxorubicin

Fractional tumor volume (FTV)[b] relative to untreated controls

| Day[a] | SN6j | DOX | Combination treatment Expected[c] | Observed | Ratio of expected:observed FTV[d] |
|---|---|---|---|---|---|
| 4 | 0.968 | 0.954 | 0.924 | 0.968 | 0.955 |
| 7 | 0.941 | 0.741 | 0.697 | 0.830 | 0.840 |
| 9 | 0.912 | 0.895 | 0.816 | 0.836 | 0.976 |
| 11 | 0.843 | 0.956 | 0.806 | 0.845 | 0.954 |
| 13 | 0.828 | 0.860 | 0.712 | 0.717 | 0.993 |
| 15 | 0.870 | 0.976 | 0.849 | 0.751 | 1.130 |
| 17 | 0.794 | 0.813 | 0.646 | 0.564 | 1.144 |
| 19 | 0.733 | 0.873 | 0.640 | 0.537 | 1.191 |

[a]Day after tumor cell inoculation. Tumor volume was measured twice or three times a week for each mouse.
[b]FTV, calculated as mean tumor volume experimental/mean tumor volume control.
[c](Mean FTV of SN6j) × (mean FTV of DOX)
[d]Obtained by dividing the expected FTV by the observed FTV. A ratio of >1 indicates a synergistic effect, and a ratio of <1 indicates a less than additive effect.

The results demonstrate a synergistic anti-tumor effect of an anti-EDG antibody and an anti-tumor agent, as SN6j and DOX exert synergistic anti-tumor efficacy in the present colon tumor model.

In further analysis of the animal test results, we found that the synergistic effect is more pronounced for mice with larger tumors compared with those with smaller tumors at the onset of the therapy. The analysis results are shown in FIG. 12 and Table 4.

Potential synergy between SN6j and DOX for suppressing growth of larger colon tumors (>4 mm$^3$) at the onset of therapy was evaluated by the method described for Table 3. Results are shown in Table 4 which summarizes relative tumor volume of treated groups versus control group on eight different time points during the therapy. Combination therapy using SN6j and DOX showed more than additive effect on tumor growth suppression. On day 13, 9 days after therapy initiation, there was a slight improvement in anti-tumor activity in the combination group when compared with the expected additive effect. This improvement became greater during the course of therapy. On days 17 and 19, there were 1.31-fold and 1.41-fold improvements, respectively, in the combination group compared with the expected additive effect (Table 4). This supraadditive effect of the combination therapy persisted until the end of experiment (i.e., day 19). These results show that SN6j and DOX exert synergistic anti-tumor efficacy against established colon tumors.

TABLE 4

Synergistic Antitumor Efficacy of SN6j Plus DOX against Colon-26 tumors of >4 mm$^3$ Fractional tumor volume (FTV)[b] relative to untreated controls

| Day[a] | SN6j | DOX | Combination treatment Expected[c] | Observed | Ratio of expected:observed FTV[d] |
|---|---|---|---|---|---|
| 4 | 0.986 | 0.979 | 0.965 | 0.992 | 0.974 |
| 7 | 0.908 | 0.753 | 0.684 | 0.800 | 0.855 |
| 9 | 0.919 | 0.954 | 0.877 | 0.884 | 0.992 |
| 11 | 0.836 | 1.018 | 0.851 | 0.934 | 0.911 |
| 13 | 0.897 | 1.009 | 0.904 | 0.799 | 1.131 |
| 15 | 0.866 | 1.159 | 1.003 | 0.854 | 1.175 |
| 17 | 0.846 | 0.954 | 0.807 | 0.618 | 1.305 |
| 19 | 0.824 | 1.101 | 0.908 | 0.645 | 1.408 |

[a]Day after tumor cell inoculation. Tumor volume was measured twice or three times a week for each mouse.
[b]FTV, calculated as mean tumor volume experimental/mean rumor volume control.
[c](Mean FTV of SN6j) × (mean FTV of DOX)
[d]Obtained by dividing the expected FTV by the observed FTV. A ratio of >1 indicates a synergistic effect, and a ratio of <1 indicates a less than additive effect.

Collectively with an earlier patent application, the presented results demonstrate synergistic anti-tumor effect of an anti-EDG antibody and an anti-tumor agent as SN6j and DOX as well as SN6j and CPA exert synergistic anti-tumor efficacy against colon cancer as well as breast cancer. This synergistic antitumor efficacy of anti-EDG mAb and a chemotherapeutic drug should be valid for solid tumors in general because anti-EDG mAbs target the tumor blood vessels which are common to all solid tumors.

REFERENCES

1. Carmeliet, P. and Jain, R. K. Angiogenesis in cancer and other diseases. Nature, 407: 249-257, 2000.
2. Folkman, J. Antiangiogenesis agents. In: V. T. DeVita, Jr., S. Hellman, and S. A. Rosenberg (ed.), Cancer: Principles & Practice of Oncology, 6th edition, pp. 509-519. Philadelphia: Lippincott, Williams & Wilkins, 2001.
3. Fidler, I. J., Kerbel, R. S., and Ellis, L. M. Biology of cancer: Angiogenesis. In: V. T. DeVita, Jr., S. Hellman, and S. V. Rosenberg (ed.), Cancer: Principles & Practice of Oncology, 6th edition, pp. 137-147. Philadelphia: Lippincott, Willimans & Wilkins, 2001.
4. Kerbel, R. S. Inhibition of tumor angiogenesis as a strategy to circumvent acquired resistance to anti-cancer therapeutic agents. Bioessays, 13: 31-36, 1991.
5. Boehm, T., Folkman, J., Browder, T., and O'Reilly, M. S. Antiangiogenic therapy of experimental cancer does not induce acquired drug resistance. Nature, 390: 404-407, 1997.
6. Dvorak, H. F., Nagy, J. A., and Dvorak, A. M. Structure of solid tumors and their vasculature: implications for therapy with monoclonal antibodies. Cancer Cells, 3: 77-85, 1991.
7. Jain, R. K. Barriers to drug delivery in solid tumors. Sci. Am., 271: 58-65, 1994.
8. Matsuzaki, H., Haruta, Y., and Seon, B. K. Effect of induced transformation of human leukemia cells on the expression of GP160, a novel human leukemia-associated cell surface glycoprotein. Fed. Proc., 46: 1056, 1987.
9. Burrows, F. J., Derbyshire, E. J., Tazzari, P. L., Amlot, P., Gazdar, A. F., King, S. W., Letarte, M., Vitetta, E. S., and Thorpe, P. E. Up-regulation of endoglin on vascular endot- 10. Seon, B. K., Matsuno, F., Haruta, Y., Kondo, M., and Barcos, M. Long-lasting complete inhibition of human solid tumors in SCID mice by targeting endothelial cells of tumor vasculature with antihuman endoglin immunotoxin. Clin. Cancer Res., 3: 1031-1044, 1997.

11. Miller, D. W., Graulich, W., Karges, B., Stahl, S., Ernst, M., Ramaswamy, A., Sedlacek, H. H., Muller, R., and Adamkiewicz, J. Elevated expression of endoglin, a component of the TGF-beta-receptor complex, correlates with proliferation of tumor endothelial cells. Int. J. Cancer, 81: 568-572, 1999.

12. Wang, J. M., Kumar, S., Pye, D., van Agthoven, A. J., Krupinski, J., and Hunter, R. D. A monoclonal antibody detects heterogeneity in vascular endothelium of tumours and normal tissues. Int. J. Cancer, 54: 363-370, 1993.

13. Fonsatti, E., Jekunen, A. P., Kairemo, K. J. A., Coral, S., Snellman, M., Nicotra, M. R., Natali, P. G., Altomonte, M., and Maio, M. Endoglin is a suitable target for efficient imaging of solid tumors: In vivo evidence in a canine mammary carcinoma model. Clin. Cancer Res., 6: 2037-2043, 2000.

14. Seon, B. K., Matsuno, F., Haruta, Y., Barcos, M., and Spaulding, B. CD105 Workshop: Immunohistochemical detection of CD105 in the vascular endothelium of human malignant and non-malignant tissues. In: T. Kishimoto, H. Kikutani, A. E. G. Kr. Von dem Borne, S. Goyert, D. Mason, M. Miyasaka, L. Moretta, K. Okumura, S. Shaw, T. A. Springer, K. Sugamura, and H. Zola (eds.), Leukocyte Typing VI: White Cell Differentiation Antigens, pp. 709-710. New York: Garland Publishing, Inc., 1998.

15. Matsuno, F., Haruta, Y., Kondo, M., Tsai, H., Barcos, M., and Seon, B. K. Induction of lasting complete regression of preformed distinct solid tumors by targeting the tumor vasculature using two new anti-endoglin monoclonal antibodies. Clin. Cancer Res., 5: 371-382, 1999.

16. Haruta, Y. and Seon, B. K. Distinct human leukemia-associated cell surface glycoprotein GP160 defined by monoclonal antibody SN6. Proc. Natl. Acad. Sci. USA, 83: 7898-7902, 1986.

17. Gougos, A. and Letarte, M. Identification of a human endothelial cell antigen with monoclonal antibody 44G4 produced against a pre-B leukemic cell line. J. Immunol., 141: 1925-1933, 1988.

18. Buhring, H. J., Muller, C. A., Letarte, M., Gougos, A., Saalmuller, A., van Agthoven, A. J., and Busch, F. W. Endoglin is expressed on a subpopulation of immature erythroid cells of normal human bone marrow. Leukemia, 5: 841-847, 1991.

19. Lastres, P., Bellon, T., Cabanas, C., Sanchez-Madrid, F., Acevedo, A., Gougos, A., Letarte, M., and Bernabeu, C. Regulated expression on human macrophages of endoglin, an Arg-Gly-Asp-containing surface antigen. Eur. J. Immunol., 22: 393-397, 1992.

20. Rokhlin, O. W., Cohen, M. B., Kubagawa, H., Letarte, M., and Cooper, M. D. Differential expression of endoglin on fetal and adult hematopoietic cells in human bone marrow. J. Immunol., 154: 4456-4465, 1995.

21. Cheifetz, S., Bellon, T., Cales, C., Vera, S., Bernabeu, C., Massague, J., and Letarte, M. Endoglin is a component of the transforming growth factor-beta receptor system in human endothelial cells. J. Biol. Chem., 267: 19027-19030, 1992.

22. Li, D. Y., Sorensen, L. K., Brooke, B. S., Urness, L. D., Davis, E. C., Taylor, D. G., Boak, B. B., and Wendel, D. P. Defective angiogenesis in mice lacking endoglin. Science, 284: 1534-1537, 1999.

23. Tabata, M., Kondo, M., Haruta, Y., and Seon, B. K. Antiangiogenic radioimmunotherapy of human solid tumors in SCID mice using $^{125}$I-labeled anti-endoglin monoclonal antibodies. Int. J. Cancer, 82: 737-742, 1999.

24. Dighiero, G. Autoreactive B-cell repertoire. In: C. Bona and A. Kaushik (eds.), Molecular Immunobiology of Self Reactivity, pp. 39-60, New York, Marcel Dekker, 1992.

25. Takahashi, N., Kawanishi-Tabata, R., Haba, A., Tabata, M., Haruta, Y., Tsai, H., and Seon, B. K. Association of serum endoglin with metastasis in patients with colorectal, breast, and other solid tumors, and suppressive effect of chemotherapy on the serum endoglin. Clin. Cancer Res., 7: 524-532, 2001.

26. Takahashi, N., Haba, A., Matsuno, F., and Seon, B. K. Antiangiogenic therapy of established tumors in human skin/severe combined immunodeficiency mouse chimeras by anti-endoglin (CD105) monoclonal antibodies, and synergy between anti-endoglin antibody and cyclophosphamide. Cancer Res., 61: 7846-7854, 2001.

27. O'Connell, K. A. and Edidin, M. A mouse lymphoid endothelial cell line immortalized by simian virus 40 binds lymphocytes and retains functional characteristics of normal endothelial cells. J. Immunol., 144: 521-525, 1990.

28. Kawata, A., Yoshida, M., Okazaki, M., Yokota, S., Barcos, M., and Seon, B. K. Establishment of new SCID and nude mouse models of human B leukemia/lymphoma and effective therapy of the tumors with immunotoxin and monoclonal antibody: marked difference between the SCID and nude mouse models in the anti-tumor efficacy of monoclonal antibody. Cancer Res., 54: 2688-2694, 1994.

29. Okazaki, M., Luo, Y., Han, T., Yoshida, M., and Seon, B. K. Three new monoclonal antibodies that define a unique antigen associated with prolymphocytic leukemia/non-Hodgkin's lymphoma and are effectively internalized after binding to the cell surface antigen. Blood, 81: 84-94, 1993.

30. Trucco, M., de Petris, S., Garotta, G., and Ceppellini, R. Quantitative analysis of cell surface HLA structures by means of monoclonal antibodies. Hum. Immunol., 1: 233-243, 1980.

31. Seon, B. K., Negoro, S., and Barcos, M. P. Monoclonal antibody that defines a unique human T-cell leukemia antigen. Proc. Natl. Acad. Sci. USA, 80: 845-849, 1983.

32. Yan, H. C., Juhasz, I., Pilewski, J., Murphy, G. F., Herlyn, M., and Albelda, S. M. Human/severe combined immunodeficient mouse chimeras. An experimental in vivo model system to study the regulation of human endothelial cell-leukocyte adhesion molecules. J. Clin. Invest., 91: 986-996, 1993.

33. Juhasz, I., Albelda, S. M., Elder, D. E., Murphy, G. F., Adachi, K., Herlyn, D., Valyi-Nagy, I. T., and Herlyn, M. Growth and invasion of human melanomas in human skin grafted to immunodeficient mice. Am. J. Pathol., 143: 528-537, 1993.

34. Brooks, P. C., Stromblad, S., Klemke, R., Visscher, D., Sarkar, F. H., and Cheresh, D. A. Antiintegrin alpha v beta 3 blocks human breast cancer growth and angiogenesis in human skin. J. Clin. Invest., 96: 1815-1822, 1995.

35. Weidner, N., Semple, J. P., Welch, W. R., and Folkman, J. Tumor angiogenesis and metastasis B Correlation in invasive breast carcinoma. N. Engl. J. Med., 324: 1-8, 1991.

36. Browder, T., Butterfield, C. E., Kraling, B. M., Shi, B., Marshall, B., O'Reilly, M. S., and Folkman, J. Antiangiogenic scheduling of chemotherapy improves efficacy against experimental drug-resistant cancer. Cancer Res., 60: 1878-1886, 2000.
37. Klement, G., Baruchel, S., Rak, J., Man, S., Clark, K., Hicklin, D. J., Bohlen, P., and Kerbel, R. S. Continuous low-dose therapy with vinblastine and VEGF receptor-2 antibody induces sustained tumor regression without overt toxicity. J. Clin. Invest., 105: R15-24, 2000.
38. Steel, G. G. Growth kinetics of tumours: Cell population kinetics in relation to the growth and treatment of cancer. Oxford: Clarendon Press, 1977.
39. Hanahan, D., Bergers, G., and Bergsland, E. Less is more, regularly: metronomic dosing of cytotoxic drugs can target tumor angiogenesis in mice. J. Clin. Invest., 105: 1045-1047, 2000.
40. Yokoyama, Y., Dhanabal, M., Griffioen, A. W., Sukhatme, V. P., and Ramakrishnan, S. Synergy between angiostatin and endostatin: Inhibition of ovarian cancer growth. Cancer Res., 60: 2190-2196, 2000.
41. Yu, D., Chen, Y. Dilley, J., Li, Y., Embry, M., Zhang, H., Nguyen, N., Amin, P., Oh, J., and Henderson, D. R. Antitumor synergy of CV787, a prostate cancer-specific adenovirus, and paclitaxel and docetaxel. Cancer Res., 61: 517-525, 2001.
42. Momparler, R. L. In vitro systems for evaluation of combination chemotherapy. Pharmacology & Therapeutics, 8: 21-35, 1980.

I claim:
1. A method for inhibiting colon tumor growth in a mammal comprising the steps of administering to the mammal according to an angiogenic schedule of drug dosing:
 i) an anti-endoglin antibody SN6j or antigen binding fragment thereof, wherein the anti-endoglin antibody SN6j is produced by a hybridoma designated by American Type Culture Collection Deposit No. HB-12171; and
 ii) a chemotherapeutic agent selected from the group consisting of cyclophosphamide or doxorubicin,
 wherein the combination of the anti-endoglin antibody SN6j or antigen binding fragment thereof and the chemotherapeutic agent has a synergistic effect on the inhibition of the colon tumor growth.
2. The method of claim 1, wherein the antigen binding fragment is selected from the group consisting of F(ab')2, Fab', Fab, Fv, Fd', Fd and single chain Fv.
3. The method of claim 1, wherein the anti-endoglin antibody SN6j and the chemotherapeutic agent are administered sequentially.
4. The method of claim 1, wherein the anti-endoglin antibody SN6j and the chemotherapeutic agent are administered simultaneously.
5. The method of claim 1, wherein the chemotherapeutic agent is cyclophosphamide.
6. The method of claim 1, wherein the chemotherapeutic agent is doxorubicin.

\* \* \* \* \*